United States Patent
Yamakawa et al.

(10) Patent No.: US 9,943,281 B2
(45) Date of Patent: Apr. 17, 2018

(54) X-RAY CT APPARATUS

(71) Applicant: Hitachi, Ltd., Tokyo (JP)

(72) Inventors: Keisuke Yamakawa, Tokyo (JP); Shinichi Kojima, Tokyo (JP); Yushi Tsubota, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 31 days.

(21) Appl. No.: 14/898,280

(22) PCT Filed: Jul. 23, 2014

(86) PCT No.: PCT/JP2014/069483
§ 371 (c)(1),
(2) Date: Dec. 14, 2015

(87) PCT Pub. No.: WO2015/012323
PCT Pub. Date: Jan. 29, 2015

(65) Prior Publication Data
US 2016/0143606 A1 May 26, 2016

(30) Foreign Application Priority Data

Jul. 25, 2013 (JP) .................................. 2013-154465

(51) Int. Cl.
*A61B 6/00* (2006.01)
*A61B 6/03* (2006.01)

(52) U.S. Cl.
CPC .......... *A61B 6/5258* (2013.01); *A61B 6/032* (2013.01); *A61B 6/4078* (2013.01); *A61B 6/5205* (2013.01)

(58) Field of Classification Search
None
See application file for complete search history.

(56) References Cited

U.S. PATENT DOCUMENTS 5,376,795 A * 12/1994 Hasegawa ............ A61B 6/5235
250/363.04
6,396,898 B1 * 5/2002 Saito .................... G01N 23/046
378/19
(Continued)

FOREIGN PATENT DOCUMENTS

| JP | 2006-025868 A | 2/2006 |
| JP | 2014-128576 A | 7/2014 |
| WO | 2013/008702 A1 | 1/2013 |

OTHER PUBLICATIONS

Wang, Jing, et al. "Penalized weighted least-squares approach to sinogram noise reduction and image reconstruction for low-dose X-ray computed tomography." IEEE transactions on medical imaging 25.10 (2006): 1272-1283.*
(Continued)

*Primary Examiner* — Michelle M Hausmann
(74) *Attorney, Agent, or Firm* — Mattingly & Malur, PC

(57) ABSTRACT

Noise of a CT image is reduced with good accuracy by using noise information obtained from the CT image. An X-ray CT apparatus comprises a successive approximate reconstruction part that reconstructs a CT image for a reconstruction area of an imaging object from measured projection data obtained by an X-ray detection part of the X-ray CT apparatus, and successively corrects the CT image so that calculated projection data obtained by forward projection of the CT image performed by calculation and the measured projection data detected by the X-ray detection part become equal to each other. The successive approximate reconstruction part comprises a noise measurement part that calculates noise intensity in the CT image at least for a predetermined region of interest, and successively corrects the CT image of the region of interest by using the calculated noise intensity.

14 Claims, 22 Drawing Sheets

(56) References Cited

U.S. PATENT DOCUMENTS

| | | | | |
|---|---|---|---|---|
| 6,876,719 B2* | 4/2005 | Ozaki | ................... | A61B 6/032 |
| | | | | 378/4 |
| 7,113,569 B2* | 9/2006 | Okumura | ............... | A61B 6/032 |
| | | | | 378/150 |
| 7,706,497 B2 | 4/2010 | Hsieh et al. | | |
| 7,889,833 B2* | 2/2011 | Hagiwara | ............. | G06T 11/008 |
| | | | | 378/4 |
| 8,290,233 B2* | 10/2012 | Noshi | ................... | A61B 6/032 |
| | | | | 382/128 |
| 9,361,686 B2* | 6/2016 | Dore | ..................... | G06T 7/0014 |
| 2005/0201513 A1* | 9/2005 | Nukui | .................... | G01T 1/164 |
| | | | | 378/19 |
| 2006/0184031 A1* | 8/2006 | Ichioka | ............... | A61B 8/0866 |
| | | | | 600/447 |
| 2008/0130824 A1* | 6/2008 | Fujisawa | ................ | A61B 6/032 |
| | | | | 378/4 |
| 2009/0232269 A1* | 9/2009 | Hsieh | .................... | A61B 6/032 |
| | | | | 378/5 |
| 2010/0046709 A1* | 2/2010 | Ueki | ..................... | A61B 6/032 |
| | | | | 378/98 |
| 2012/0155728 A1* | 6/2012 | DeMan | ................. | G06T 11/006 |
| | | | | 382/131 |
| 2012/0288178 A1* | 11/2012 | Uebayashi | ........... | A61B 6/5258 |
| | | | | 382/131 |
| 2013/0243152 A1* | 9/2013 | Hagiwara | ............ | G06T 11/005 |
| | | | | 378/19 |
| 2014/0153803 A1 | 6/2014 | Noda | | |
| 2014/0193055 A1 | 7/2014 | Takahashi et al. | | |
| 2014/0270454 A1* | 9/2014 | Chen | ...................... | G06T 5/002 |
| | | | | 382/132 |

OTHER PUBLICATIONS

Gravel, Pierre, Gilles Beaudoin, and Jacques A. De Guise. "A method for modeling noise in medical images." IEEE Transactions on medical imaging 23.10 (2004): 1221-1232.*

International Preliminary Report on Patentability received in corresponding International Application No. PCT/JP2014/069483 dated Feb. 4, 2016.

International Search Report of PCT/JP2014/069483.

* cited by examiner (a)　　　　　　　　(b)

FIG. 13
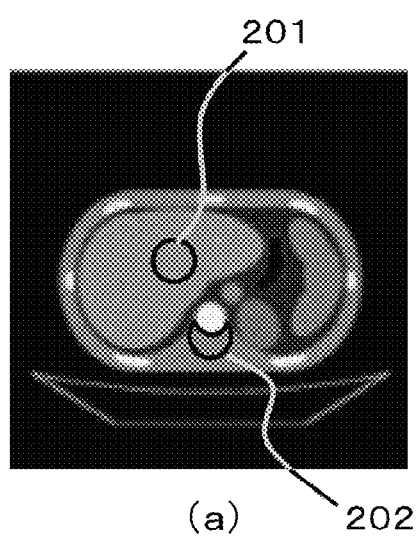 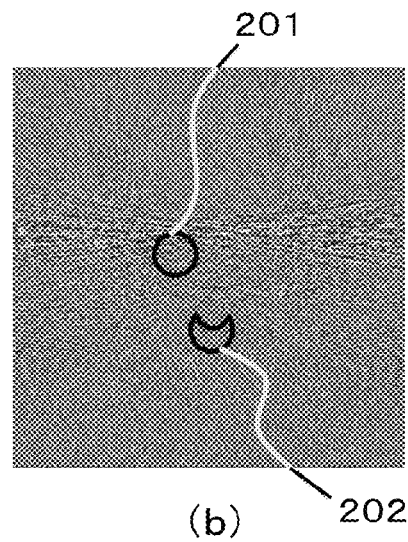
(a)　　　　　　　　　(b)

(a)  (b)

X-RAY CT APPARATUS

TECHNICAL FIELD

The present invention relates to an X-ray CT apparatus, especially a technique for calculating distribution of noise contained in a CT image, and generating a CT image from which the noise is removed.

BACKGROUND ART

X-Ray CT (computed tomography) apparatuses are apparatuses for calculating X-ray absorption coefficients at positions of an imaging object from measured projection data obtained by capturing images of the imaging object from many directions, and obtaining an image of X-ray absorption coefficient distribution (henceforth also referred to as CT image). By replacing the X-ray absorption coefficients with normalized CT values (−1000 for air, and 0 for water), a CT image is generated.

The CT image shows a tomographic image of a subject. On medical sites, pathological conditions of patients can be accurately and instantly diagnosed by using CT images, and therefore they are clinically useful. However, in order to obtain a CT image of high image quality required for diagnosis by medical practitioners, radiation exposure of a certain extent is unavoidable. If the irradiation dose is reduced in order to realize low exposure, ratio of noise to the detected signals increases, and there are thereby generated many line-shaped streak artifacts and grain-like noise, which cause incorrect diagnoses. Therefore, it has been desired to simultaneously realize both diagnosis of good quality and low radiation exposure by reducing the streak artifacts and noises at the time of low radiation dose imaging.

Patent document 1 discloses a method for generating a noise map in which image of imaging object has been removed (difference image). In this method, a plurality of measured projection data obtained by scanning the same positions of one imaging object at substantially the same times are divided into two sets of projection data according to projection angles, CT images are reconstructed from the sets of the divided projection data, respectively, a difference image of the two CT images is obtained, and a noise map is obtained from this difference image. According to the technique of Patent document 1, a filter is created by using this noise map to remove noise of the CT image. In this method, the filter is created on the basis of the noise map obtained from actual CT images, and therefore image of the imaging object is less easily degraded compared with the case of using a conventional filter for eliminating radio frequency components.

PRIOR ART REFERENCES

Patent Document

Patent document 1: U.S. Pat. No. 7,706,497

SUMMARY OF THE INVENTION

Object to be Achieved by the Invention

According to the technique of Patent document 1, in order to obtain a noise map, the measured projection data obtained with a plurality of projection angles are divided into two. However, the number of times of imaging per rotation (projection angles) is determined so that when a CT image is reconstructed by using measured projection data of all the projection angles, a CT image containing less artifacts can be reconstructed, and therefore if a CT image is reconstructed from measured projection data divided into two, artifacts increase to an unignorable level. In particular, in peripheral regions of CT image remote from the rotation center of the CT apparatus, density of passing routes of X-rays (interval of data) are sparse, and therefore influence of artifacts becomes more significant. Therefore, in a noise map obtained by computing difference of CT images obtained from measured projection data divided into two sets according to projection angles as described in Patent document 1, errors of noise values becomes large in the peripheral regions of the image. Therefore, if noise in a CT image is reduced by a filter processing using such a noise map, accuracy of the peripheral regions of the image is degraded.

An object of the present invention is to reduce noise of a CT image with good accuracy.

Means for Achieving the Object

In order to achieve the aforementioned object, according to the first embodiment of the present invention, a noise measurement part that calculates noise intensity for at least a predetermined region of interest in a CT image reconstructed from measured projection data is provided, and the CT image of the region of interest is successively corrected by using the noise intensity calculated by the noise measurement part.

In the second embodiment of the present invention, a noise measurement part that calculates noise intensity of a CT image for a region of interest by dividing measured projection data for at least one direction among the channel direction and slice direction is provided. Noise of the CT image of the region of interest is reduced by using the noise intensity calculated by the noise measurement part.

Effect of the Invention

According to the first embodiment of the present invention, by selectively correcting CT values of noises contained in a CT image of an imaging object, the noises of the CT image can be reduced. According to the second embodiment, by reducing image degradation due to influences of artifacts, noise can be reduced with good accuracy.

BRIEF DESCRIPTION OF THE DRAWINGS

FIG. 13 includes (a) an explanatory drawing showing a CT image and a shape of an optimized region of interest, and (b) an explanatory drawing showing a corrected difference image and a region of interest according to the embodiment 5.

MODES FOR CARRYING OUT THE INVENTION

Hereafter, embodiments of the present invention will be explained.

<Embodiment 1>

Figure 1:
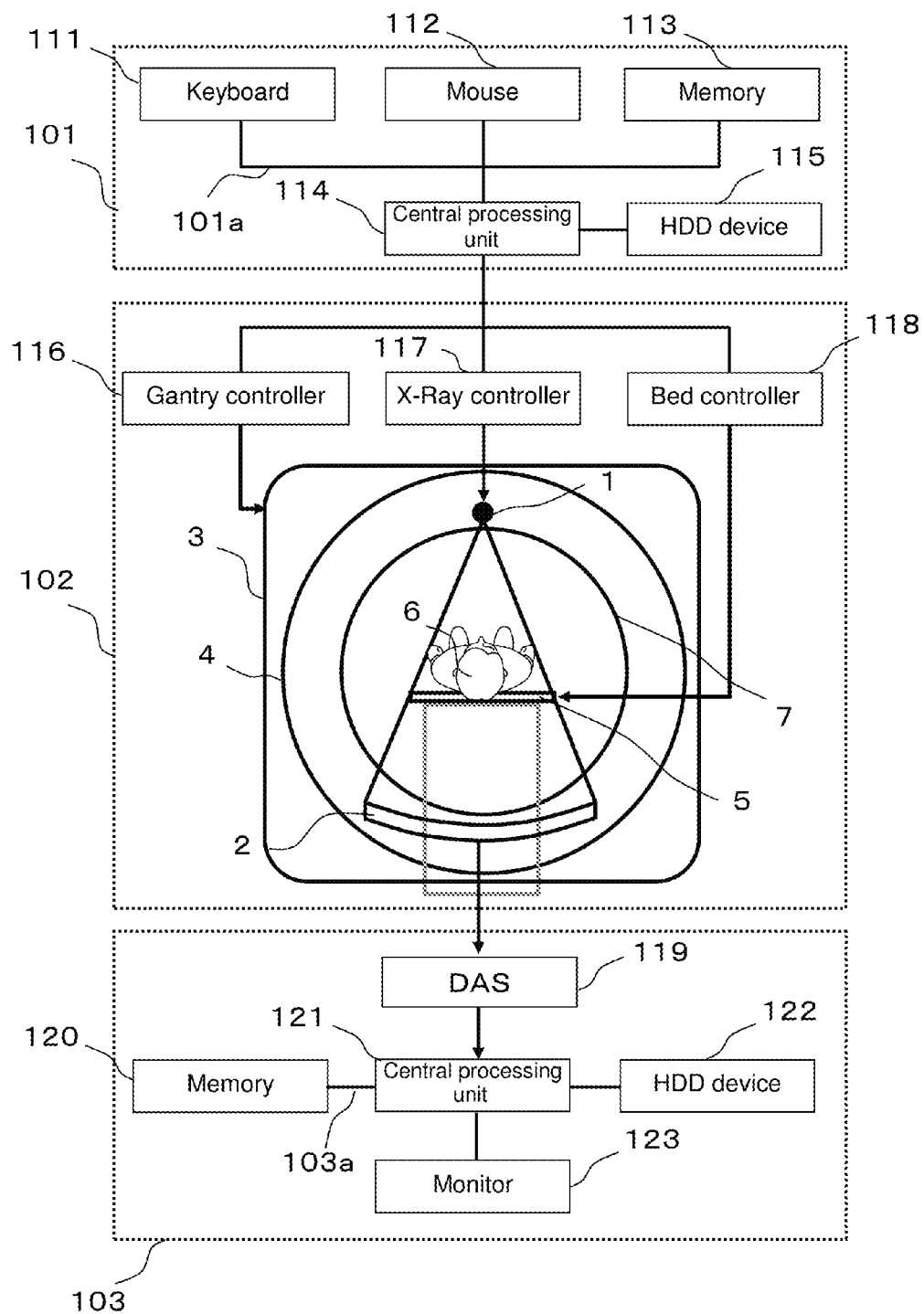
FIG. 1 is a block diagram for explaining configurations of hardware of parts of an X-ray CT apparatus according to the embodiment 1.
Figure 2:
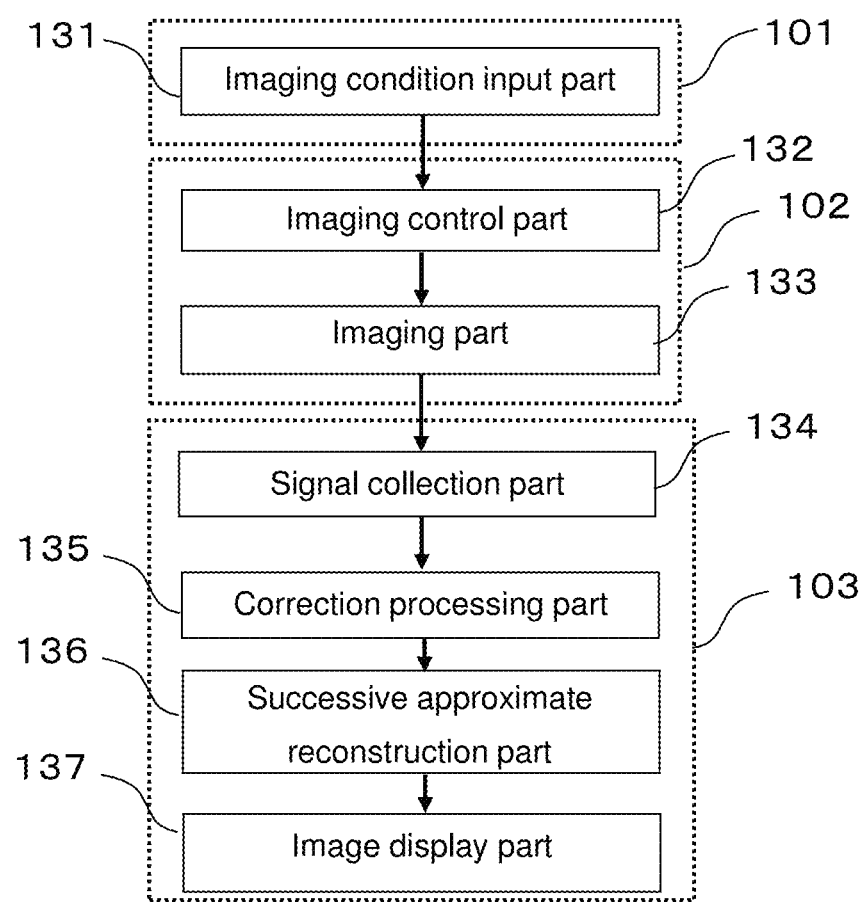
FIG. 2 is a functional block diagram of the X-ray CT apparatus according to the embodiment 1.

The X-ray CT apparatus of the present invention comprises, as shown in FIGS. 1 and 2, an X-ray generation part 1 that generates X-rays, an X-ray detection part 2 that detects X-rays having transmitted through an imaging object to obtain measured projection data, a rotation plate 4 that carries the X-ray generation part 1 and the X-ray detection part 2 and rotates around the imaging object, and a successive approximate reconstruction part 136. The successive approximate reconstruction part 136 reconstructs a CT image for a reconstruction area of the imaging object from the measured projection data obtained by the X-ray detection part, obtains calculated projection data by performing forward projection of the CT image by calculation, and successively corrects the CT image so that the calculated projection data and the measured projection data become equal to each other. In the successive approximate reconstruction part 136, the noise measurement part 151 that calculates noise intensity in the CT image at least for a predetermined region of interest is disposed. The successive approximate reconstruction part 136 successively corrects the CT image of the region of interest using the noise intensity calculated by the noise measurement part 151.

By introducing the noise measured from the CT image into the successive approximate reconstruction as described above, the noise of the CT image can be reduced without degrading the image of the imaging object contained in the CT image.

In the present invention, the imaging object means an object of the imaging, and includes a subject 6 and a bed 5 for supporting the subject 6. The subject 6 is not limited to a human body, and may be a material to be examined, such as phantom and machine.

The successive approximate reconstruction part 136 comprises a successive approximation processing part 152 that repeatedly performs calculation for correcting the CT image so that the difference of the measured projection data and the calculated projection data become small by using the difference, and prior calculation for correcting the CT image so that differences of CT values of two or more pixels become small by using the CT value differences of the two or more pixels obtained before the correction. According to the present invention, by using the noise intensity of the region of interest calculated by the noise measurement part for the prior calculation, the CT image is corrected for the region of interest. By using the noise intensity measured by the noise measurement part 151 for the prior calculation as described above, the noise can be efficiently reduced.

In the prior calculation, correction amount of a CT value of a predetermined first pixel in the region of interest is changed depending on whether the CT value difference of the first pixel and a second pixel in a predetermined positional relationship with respect to the first pixel is smaller than or larger than the noise intensity obtained for the region of interest. For example, when CT value difference of two or more pixels in the region of interest are smaller than the noise intensity of the region of interest, the CT value of the first pixel is corrected by a correction amount corresponding to the absolute value of the CT value difference, and when the CT value difference is larger than the noise intensity, the CT value of the first pixel is corrected by a predetermined correction amount irrespective of the CT value difference.

This enables selective correction of pixels of noise, and therefore noise can be reduced with suppressing degradation of the image of the imaging object in the CT image.

The noise measurement part 151 may set a plurality of regions of interest in a CT image, calculate noise intensity for each region of interest, thereby calculate distribution of noise intensity for the whole CT image, and generate a noise image that represents distribution of noise intensity. By obtaining a noise image of the whole CT image as described above, it becomes possible to perform noise reduction processing for the whole CT image.

Figure 4:
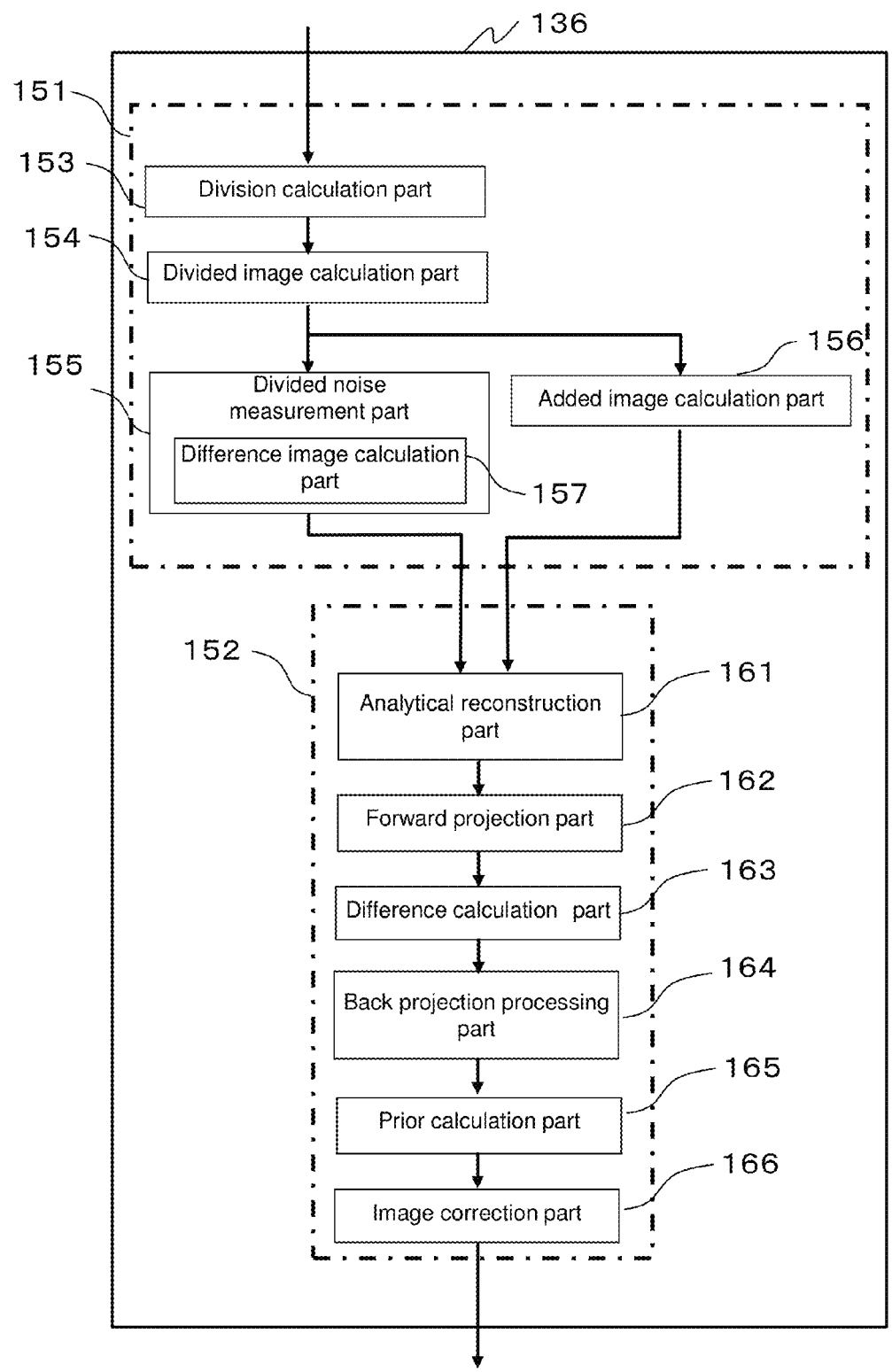
FIG. 4 is a functional block diagram for explaining function of a successive approximate reconstruction part 136 according to the embodiment 1.

The noise measurement part 151 has a configuration comprising, for example, as shown in FIG. 4, a division calculation part 153 that divides the measured projection data into M of data sets (M is 2 or larger), a divided image calculation part 154 that reconstructs a CT image for each of M sets of the measured projection data divided by the division calculation part 153, and a divided noise measurement part 155 that obtains difference images of M of CT images reconstructed by the divided image calculation part 154, and calculates variation of the CT values of the regions of interest in the difference images as noise intensity.

Hereafter, the X-ray CT apparatus of the embodiment 1 will be more specifically explained with reference to the drawings.

FIG. 1 shows hardware configuration of an X-ray CT apparatus according to the embodiment 1. This X-ray CT apparatus carries the successive approximate reconstruction part 136 as software as described later, but a part or all of the successive approximate reconstruction part 136 can also be constituted by hardware using a programmable integrated circuit such as ASIC (application specific integrated circuit) or FPGA (field-programmable gate array). FIG. 2 is a functional block diagram of the X-ray CT apparatus shown in FIG. 1.

The X-ray CT apparatus shown in FIG. 1 comprises an input part 101 for inputting imaging conditions such as X-ray irradiation conditions and conditions of image reconstruction, an imaging part 102 that performs control of imaging, irradiation and detection of X-rays, and an image generation part 103 that performs correction of detected signals and image reconstruction to output an image. The input part 101 and the image generation part 103 do not necessarily need to be integrally constituted with the main body of the apparatus comprising the imaging part 102, and they may be disposed in a place remote from the imaging part 102, and connected via a network. The input part 101 and the image generation part 103 may share hardware for realizing the aforementioned configuration such as the input and output parts, processing part, and storage part.

As shown in FIG. 2, the input part 101 functions as an imaging condition input part 131 for inputting imaging conditions. The imaging part 102 functions as an imaging control part 132 that controls imaging on the basis of the imaging conditions inputted from the imaging condition input part 131, and an imaging part 133 that performs irradiation and detection of X-rays. The image generation part 103 functions as a signal collection part 134 that converts the detected signals into digital signals, a correction processing part 135 that corrects the digital signals, a successive approximate reconstruction part 136 that performs image reconstruction with the corrected projection data, and an image display part 137 that outputs a reconstructed CT image.

As shown in FIG. 1, the input part 101 has a keyboard 111 and a mouse 112 for input of imaging conditions etc. It may further comprise other input means such as pen tablet or touch panel, although they are not shown in the drawing. The input part 101 further comprises a central processing unit (CPU) 114, a storage part consisting of a memory 113, HDD (hard disk drive) device 115, or the like, and a monitor not shown in the drawing. The parts are connected with a data bus 101a. Data inputted from the keyboard 111 or the like are received by the CPU 114 as a processing part. The CPU 114 reads and executes a predetermined program stored in advance in the memory 113, HDD device 115, or the like to function as the imaging condition input part 131 shown in FIG. 2. The CPU 114 reads and executes another program to send control signals to the imaging part 102, and thereby also functions as a part of the imaging control part 132 shown in FIG. 2.

The imaging part 102 shown in FIG. 1 is constituted by a gantry 3, the bed 5 that supports the subject 6, an X-ray controller 117, a gantry controller 116, and a bed controller 118. The gantry 3 comprises an X-ray tube (X-ray generation part) 1, an X-ray detector (X-ray detection part) 2, and the rotation plate 4 that carries them. A circular opening 7 is provided at the center of the gantry 3 and the rotation plate 4, and the bed 5 is inserted into the opening 7. The gantry controller 116, the X-ray controller 117, and the bed controller 118 function as the imaging control part 132 shown in FIG. 2. The gantry 3 and the bed 5 function as the imaging part 133 shown in FIG. 2.

The X-ray tube 1 and the X-ray detector 2 realize irradiation of X-rays on the subject 6 and detection of them. Distance between X-ray generation point of the X-ray tube 1 and X-ray entering surface of the X-ray detector 2 is typically 1000 [m]. Diameter of the opening 7 is typically 700 [mm]. Time required for one rotation of the rotation plate 4 is 1.0 [s]. The X-ray detector 2 comprises known X-ray detection elements consisting of scintillator, photodiode, etc., and the X-ray detection elements are disposed along the channel direction (direction along a circle that maintains the same distance from the X-ray tube 1 in a plane parallel to the main plane of the rotation plate 4), and the slice direction (body axis direction of the subject 6). Number of the X-ray detection elements along the channel direction (henceforth referred to as channel number) is, for example, 1000. Size of each X-ray detection element for the channel direction is typically 1 [mm]. The number of times of imaging performed by the imaging part 102 in one rotation of the rotation plate 4 is 900, and one imaging is performed whenever the rotation plate 4 rotates 0.4 degree. The angle of the rotation plate 4 at the time of performing imaging is referred to as projection angle. These specifications are not limited to those values mentioned above, and can be variously changed depending on the configuration of the X-ray CT apparatus.

The gantry controller 116 controls the rotation operation of the rotation plate 4. The X-ray controller 117 controls the operation of the X-ray tube 1. The bed controller 118 controls the position of the bed 5.

The image generation part 103 comprises a data acquisition system (DAS) 119, a central processing unit (CPU) 121, a storage part consisting of a memory 120, HDD device 122, or the like, and a monitor 123. These are connected with a data bus 103a. The DAS 119 functions as the signal collection part 134 shown in FIG. 2. The CPU 121 reads and executes a predetermined program stored beforehand in the memory 120, HDD device 122, or the like to function as the correction processing part and the successive approximate reconstruction part 136 shown in FIG. 2. The monitor 123 functions as the image display part 137.

Signals detected by the X-ray detector 2 of the imaging part 102 are collected by the DAS 119, which functions as the signal collection part 134, converted into digital signals, and sent to and received by the CPU 121. The CPU 121 performs correction, and image reconstruction by using successive approximation processing. The data are stored in the HDD device 122, or the like, and outputted and inputted outside, if needed. The reconstructed CT image is displayed on the monitor 123 consisting of a liquid crystal display, CRT, etc. that functions as the image display part 137. The CPU 121, memory 120, monitor 123, and so forth can be shared with the input part 101 as described above.

Figure 3:
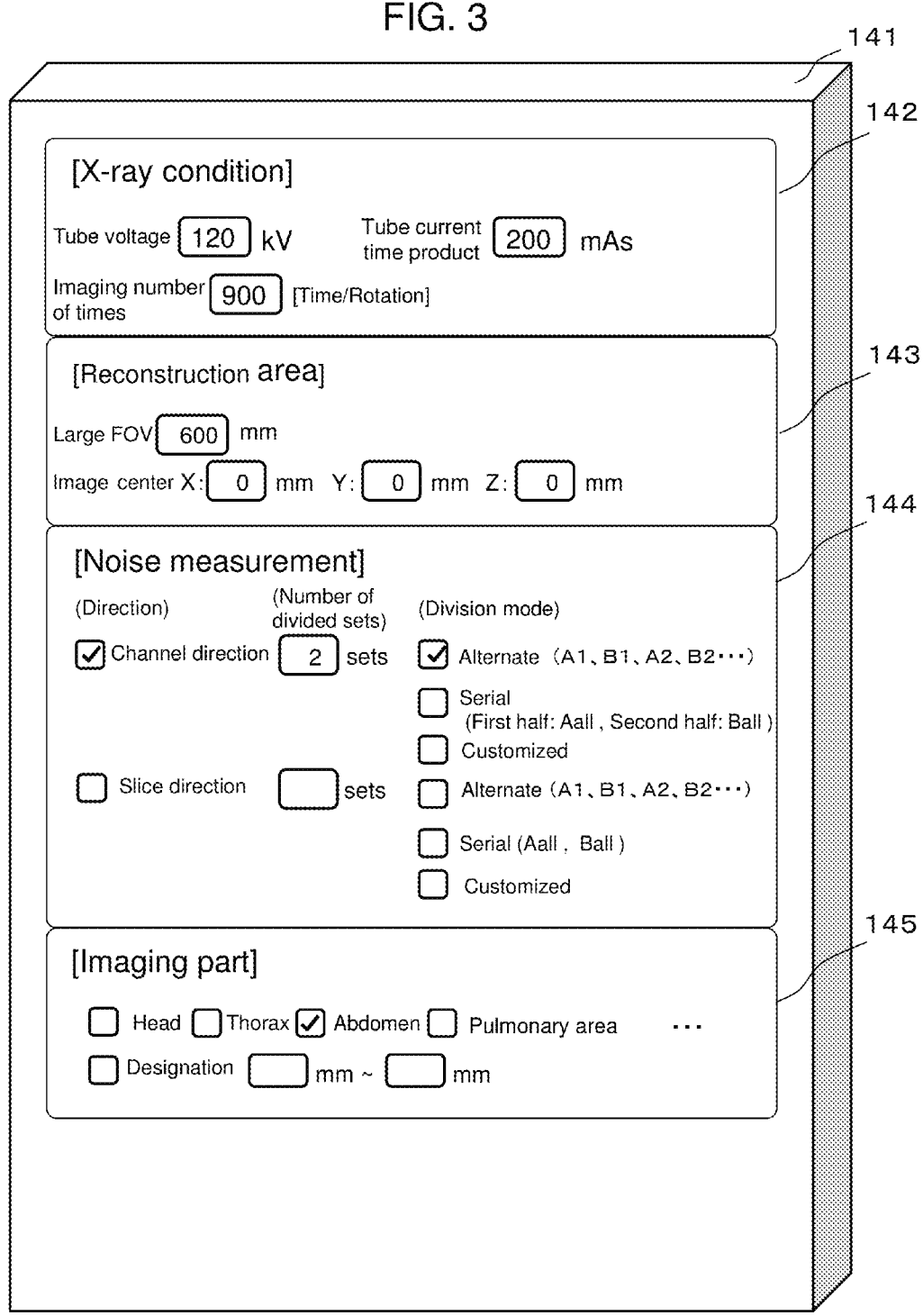
FIG. 3 is an explanatory drawing for explaining an imaging condition reception screen 141 of an imaging condition input part 131 according to the embodiment 1.

Hereafter, flow of the imaging operation performed by the X-ray CT apparatus of the embodiment 1 will be explained with reference to mainly the functional block diagram of FIG. 2, together with the hardware configuration shown in of FIG. 1, and FIG. 3. FIG. 3 shows an example of an imaging condition reception screen 141 displayed on the monitor 123 of the imaging condition input part 131.

The imaging condition input part 131 shown in FIG. 2 displays the imaging condition reception screen 141 shown in FIG. 3 on the monitor 123, and receives input of an operator. The imaging condition reception screen 141 shown in FIG. 3 includes an X-ray condition setting region 142 for setting tube voltage and tube current time product corresponding to energy and output of X-ray to be irradiated, and the number of times of imaging in one rotation, a reconstruction area setting region 143 for setting the area of reconstructed image, a noise measurement setting region 144 for selecting conditions required for measuring noises of a CT image, and an imaging part setting region 145 for setting an imaging part.

The operator sets X-ray conditions on the X-ray condition setting region 142, reconstruction area on the reconstruction area setting region 143, noise measurement conditions on the noise measurement setting region 144, and imaging part on the imaging part setting region 145 by using the mouse 112, keyboard 111, or the like, with looking at the imaging condition reception screen 141. Hereafter, these operations will be explained in more detail.

FIG. 3 shows an example in which a tube voltage value of 120 [kV], tube current time product of 200 [mAs], and number of times of imaging of 900 [time/rotation] are set on the X-ray condition setting region 142 by the operator. FIG. 3 shows an example using X-rays having one kind of energy spectrum. In the case of multi-energy CT using X-rays of two or more kinds of energy spectra, input spaces for tube voltage, tube current time product, and number of times of imaging are additionally provided in the X-ray condition setting region 142, and they are similarly set for every kind of X-ray.

On the reconstruction area setting region 143 shown in FIG. 3, the operator sets the reconstruction area (FOV), which is a region for which image reconstruction is performed. The reconstruction area setting region 143 shown in FIG. 3 has a configuration that the reconstruction area is set by setting size and center position of FOV. In this embodiment, FOV is defined as a square, as an example. In the example shown in FIG. 3, a side length of 600 [mm] is set for FOV, and the center position of FOV is set at the position of X=Y=Z=0 [mm], which corresponds to the rotation center. However, FOV is not limited to a square, and may be set in an arbitrary shape, such as circle, rectangle, cube, rectangular parallelepiped, and sphere. The present invention can also be applied to such cases.

The noise measurement setting region 144 is a region for setting the method for measuring noises of the CT image described later. According to the embodiment 1, in order to calculate noises contained in a CT image from measured projection data, the measured projection data are divided for the channel direction, or the slice direction. As conditions for performing this division, the direction for the division, number of sets into which the data are to be divided, and division method are set on the noise measurement setting region 144. The direction for the division is chosen from the channel direction and the slice direction. The number of divided data sets is set to be a number of 2 or larger. The method for the division is selected from, for example, a method of dividing data so that they alternately belong to different sets, a method of dividing data into those of the first half and those of the second half, and a method of dividing measured projection data into an arbitrary part of them and the other data. In the example shown in FIG. 3, the channel direction is selected as the direction for the division, 2 is selected as the number of the sets of the divided data, and the method of dividing data so that they alternately belong to different data sets is selected.

The imaging part setting region 145 shown in FIG. 3 sets an imaging part by selecting an object of the X-ray irradiation (part such as head, thorax, or pulmonary area, or tissue), or numerically defining the X-ray irradiation area. In the example shown in FIG. 3, the abdominal part is chosen.

The imaging condition reception screen 141 is not limited to the screen configuration shown in FIG. 3. It is also possible to employ a configuration that combinations of the X-ray conditions, reconstruction area, reconstruction conditions, and conditions for setting an imaging part, of which setting is received on the imaging condition reception screen 141, are stored in advance in the HDD device 115, and they are read out by the imaging condition input part 131 from the HDD device 115. In this case, the operator does not need to input the X-ray conditions etc. each time. Furthermore, it is also possible to employ a configuration that a plurality of kinds of combinations of the aforementioned conditions to be set are stored in advance, and the operator chooses one from the plurality of kinds of them.

Then, the imaging part 102 shown in FIG. 2 performs X-ray imaging according to the imaging conditions received by the imaging condition input part 131. If the operator directs start of imaging by using the mouse 112, keyboard 111, or the like, the CPU 114 outputs control signals to the bed controller 118 and the gantry controller 116 of the imaging control part 132. In response to the control signals, the bed controller 118 performs control for moving the bed 5 along the direction of the rotation axis of the rotation plate 4, and when the imaging part of the subject 6 comes to be within the area of passages of X-rays (imaging position) between the X-ray tube 1 and the X-ray detector 2, it stops the movement of the bed 5. Disposition of the subject 6 at the imaging position is thereby completed.

The gantry controller 116 starts the rotation of the rotation plate 4 by a driving motor at the same time as the CPU 114 directs the start of the imaging. When the rotation plate 4 comes to rotate at a constant speed, and the disposition of the subject 6 at the imaging position is completed, the CPU 114 directs X-ray irradiation timing for the X-ray tube 1, and imaging timing for the X-ray detector 2 to the X-ray controller 117. The X-ray controller 117 makes the X-ray tube 1 irradiate X-rays, and makes the X-ray detector 2 detect the X-rays according to the directions to start the imaging. The X-ray controller 117 also determines the energy spectrum and output of X-rays to be irradiated with, for example, the tube voltage and tube current time product of the X-ray tube 1 set by the operator.

In the above description, an example of using X-rays of one kind of energy spectrum is explained. However, the present invention is also applicable to the multi-energy CT. In such a case, control is performed so that X-rays of two or more kinds of energy spectra are irradiated by changing the tube voltage at high speed for every rotation or during one rotation, and imaging data are obtained.

The signal collection part 134 of the image generation part 103 converts the output signals of the X-ray detector 2 into digital signals, and saves them in the memory 120. The correction processing part 135 performs such correction as offset correction for calibrating the zero value of the detection signals of X-rays, reference correction for correcting fluctuation of signal components detected for every projection angle, and known air calibration processing for correcting sensitivities of the detection elements for the data to obtain measured projection data of the subject 6. The measured projection data are sent to the successive approximate reconstruction part 136.

Still more detailed functional configuration of the successive approximate reconstruction part 136 is shown in FIG. 4. The successive approximate reconstruction part 136 comprises the noise measurement part 151 that measures noise intensity of a CT image for at least a region of interest, and the successive approximation processing part 152 that introduces the measured noise and successively corrects the CT image. The noise measurement part 151 comprises the division calculation part 153 that divides the measured projection data, the divided image calculation part 154 that performs reconstruction from each set of the divided measured projection data, the divided noise measurement part 155 that measures noise in the divided CT images, and an added image calculation part 156 that creates an initial image for the successive approximate reconstruction. The divided noise measurement part 155 comprises a difference image calculation part 157 that obtains differences of reconstructed images for measuring noise of an image reconstructed by the divided image calculation part 154.

The successive approximation processing part 152 comprises an analytical reconstruction part 161, a forward projection part 162, a difference calculation part 163, a back projection processing part 164, a prior calculation part 165, and an image correction part 166. With such a configuration, the successive approximation processing part 152 successively corrects the CT image so that the calculated projection data obtained by forward projection of the CT image performed by calculation, and the measured projection data become equal to each other. The prior calculation part 165 adds the difference value of the CT values of pixels constituting the CT image multiplied by a coefficient to the corrected image under calculation to make differences of the CT values of the pixels smaller, and thereby reduce the noise.

According to the present invention, the noise intensity of the CT image calculated by the noise measurement part 151 is used for successive correction of the CT image of the region of interest performed by the successive approximation processing part 152. Since the noise of the CT image can be thereby selectively and successively corrected, the noise of the CT image can be highly precisely removed, and degradation of the image other than the noise such as the image of the imaging object can be prevented. Specifically, in this embodiment, calculation in the prior calculation part 165 is performed by using the noise intensity measured by the noise measurement part 151.

Figure 5:
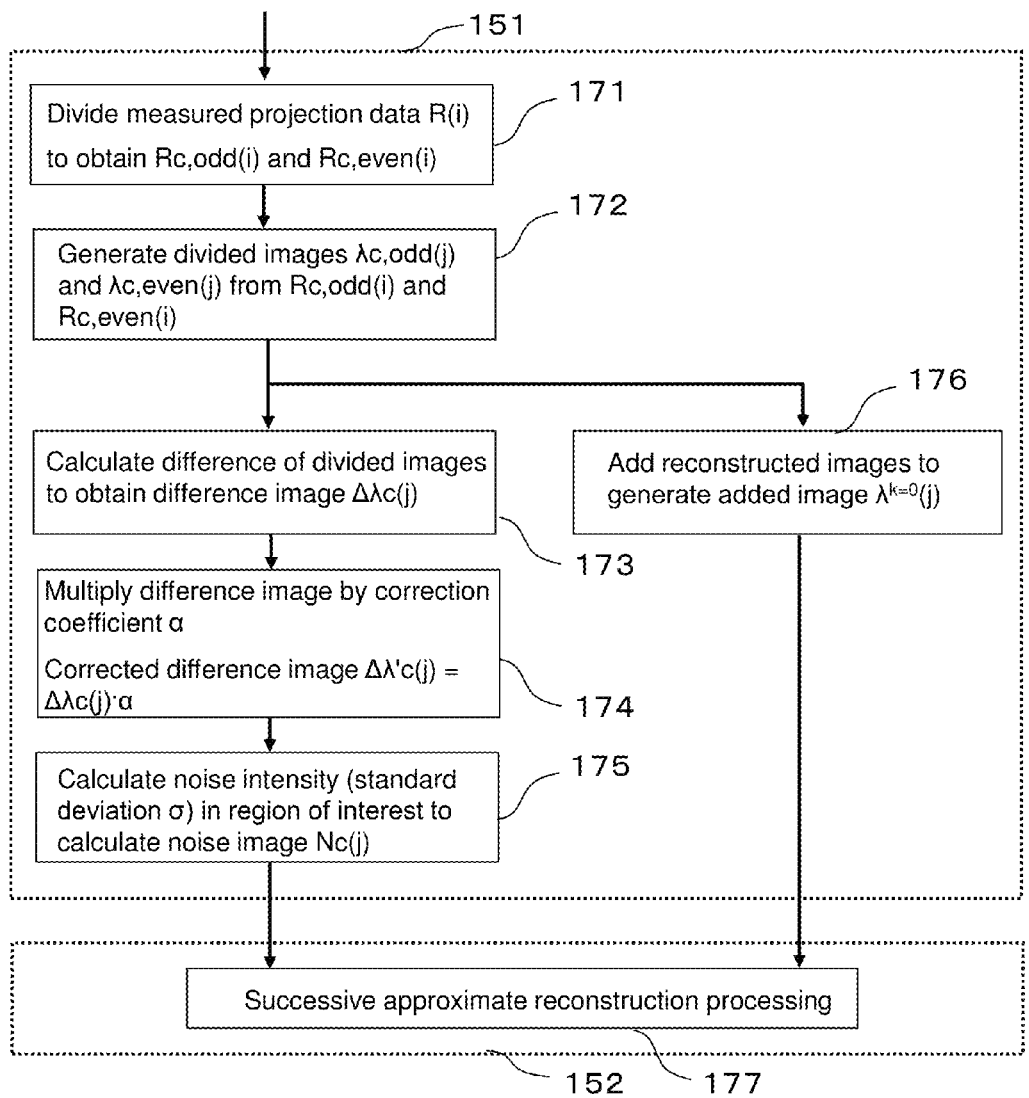
FIG. 5 is a flowchart for explaining procedure of calculation performed by a noise measurement part 151 according to the embodiment 1.
Figure 7:
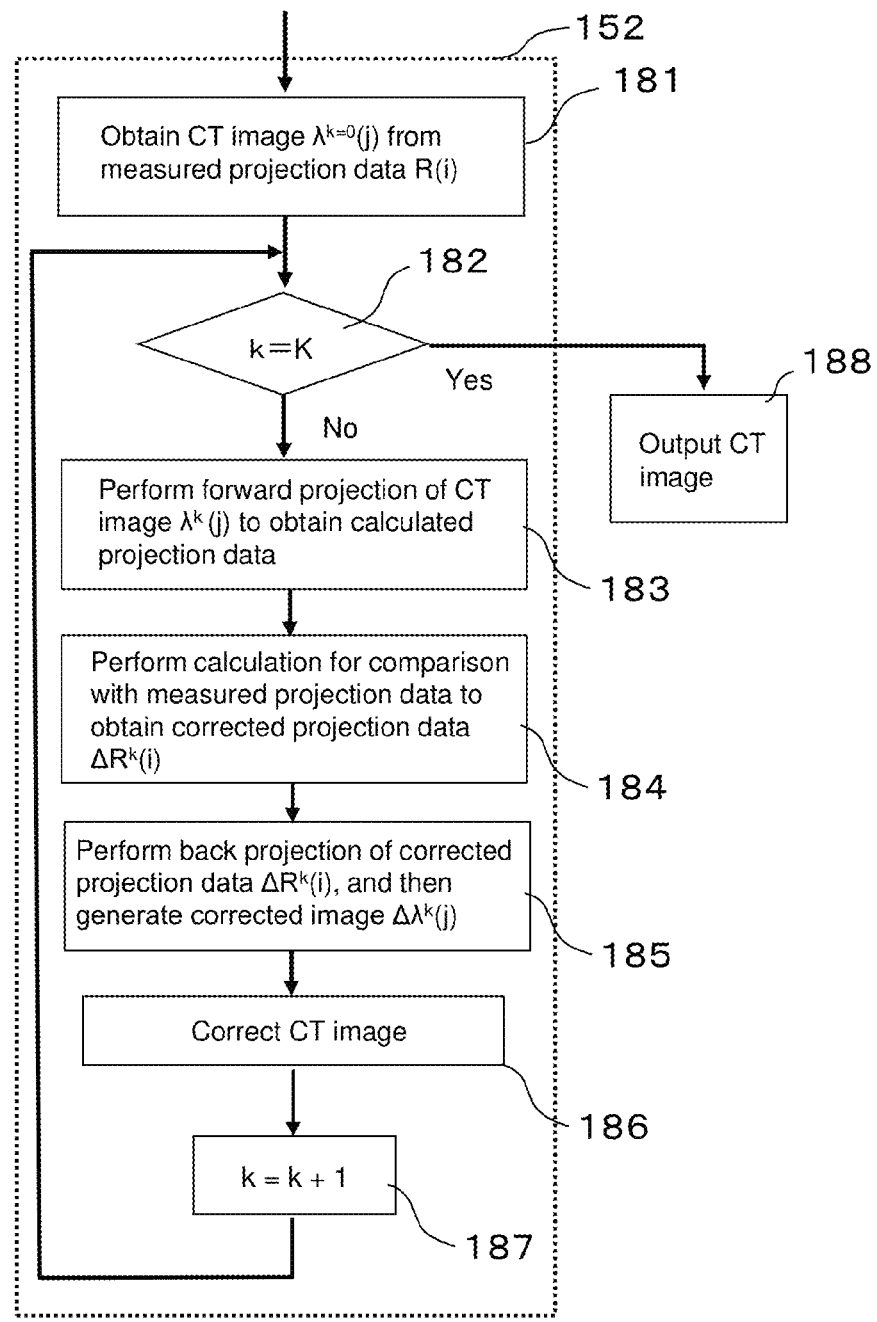
FIG. 7 is a flowchart for explaining the calculation procedure performed by the successive approximate reconstruction method according to the embodiment 1.

These functional blocks operate as shown in the flowcharts of FIGS. 5 and 7. Hereafter, they will be explained in detail.

Figure 6:
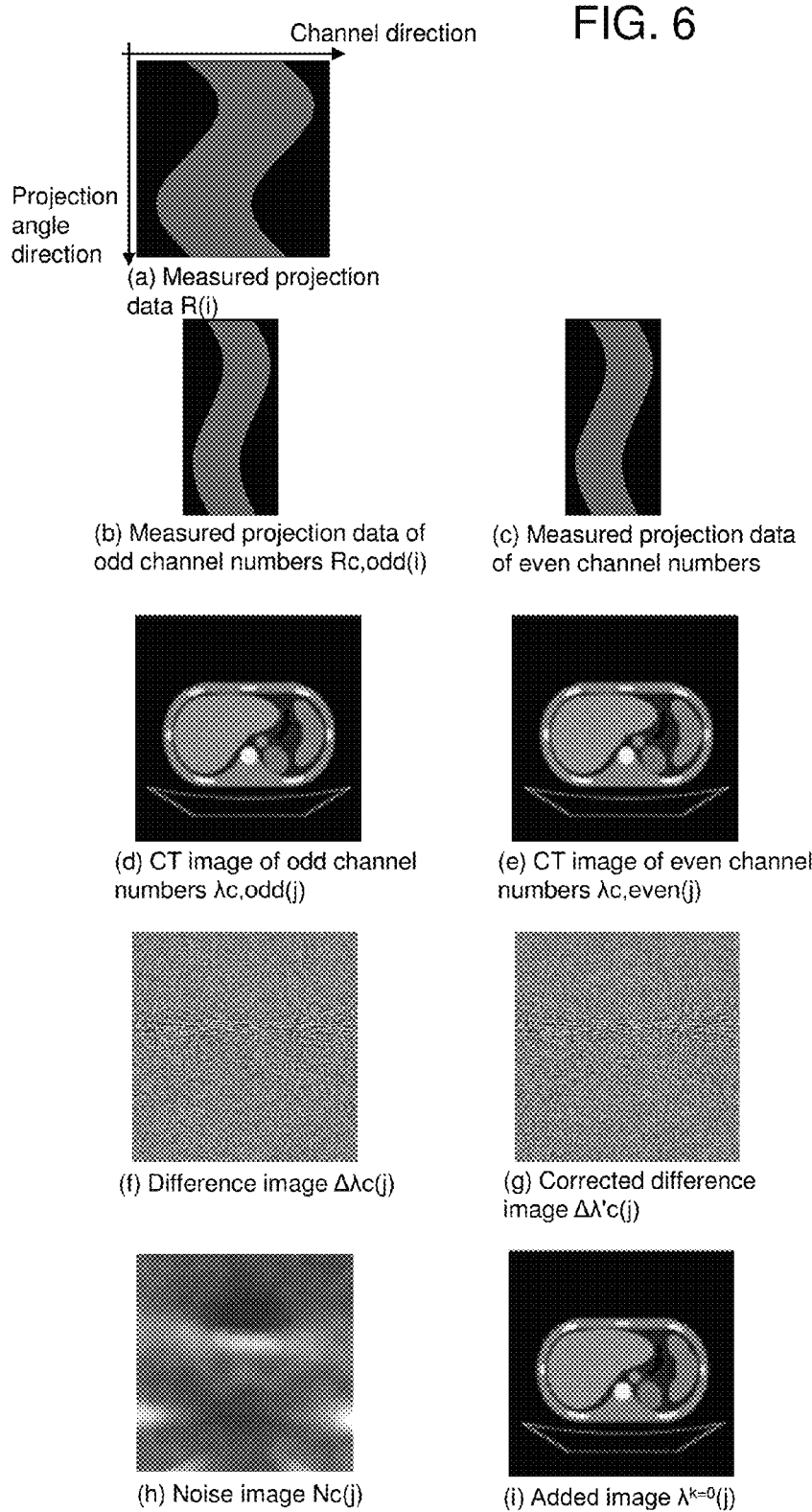
FIGS. 6, (a) to (i) are explanatory drawings for explaining results of the calculation performed by the noise measurement part 151 according to the embodiment 1.

In the step 171 shown in FIG. 5, the division calculation part 153 shown in FIG. 4 divides measured projection data $R(i)$ into two or more sets for the channel direction. Hereafter, there will be explained an example of dividing the data into a set of measured projection data $R_{c,odd}(i)$ obtained with detection elements of odd numbers, and a set of measured projection data $R_{c,even}(i)$ obtained with detection elements of even numbers. The symbol i represents number of the detection element of the X-ray detector 2. FIG. 6, (a) shows measured projection data $R(i)$ for 1000 channels as an example. In FIG. 6, (a), the horizontal axis indicates channel number, and the vertical axis indicates projection angle (rotation angle of the X-ray tube 1 and the X-ray detector 2). Density of the measured projection data shown in FIG. 6, (a) represents value of each pixel (CT value). FIG. 6, (b) shows the divided measured projection data $R_{c,odd}(i)$ of the odd numbers, and FIG. 6, (c) shows the measured projection data $R_{c,even}(i)$ of even numbers. Since the data shown in FIGS. 6, (b) and (c) are obtained by dividing the measured projection data $R(i)$ shown in FIG. 6, (a) into two sets of data for the channel direction, channel number of each set is 500.

In this step 171, the channel numbers of the divided measured projection data $R_{c,odd}(i)$ and $R_{c,even}(i)$ may be increased to the number before the division by interpolating data between the channels. For example, lacking data between adjacent channels after division are calculated by a known interpolation method from values of the measured projection data of the channels after the division. As the interpolation method, for example, linear interpolation such as averaging, or nonlinear interpolation such as spline interpolation is used. Alternatively, value of a channel in the vicinity of a channel lacking data may be used as it is as the value of the data-lacking channel. If such an interpolation processing as mentioned above is performed, the numbers of channels of the measured projection data $R_{c,odd}(i)$ and $R_{c,even}(i)$ after the division each increase from 500 channels to 1000 channels.

Then, in the step 172 shown in FIG. 5, the divided image calculation part 154 shown in FIG. 4 obtains CT images $\lambda_{c,odd}(i)$, and $\lambda_{c,even}(j)$, which represent CT values of the imaging object, from the measured projection data $R_{c,odd}(i)$ of odd numbers and the measured projection data $R_{c,even}(i)$ of even numbers, respectively, by calculation using an analytical reconstruction method. The symbol j represents pixel number of the CT image, and the CT image consists of J of pixels. As the analytical reconstruction method, known methods such as the Feldkamp method are used. As the CT image, not only a general two-dimensional (x, and y directions) tomographic image, but also one-dimensional data (x direction), three-dimensional data (x, y, and z directions), in which an image is overlaid along the body axis direction z, or four-dimensional data (x, y, z, t), which also uses the time direction t in addition to the three-dimensional directions, may also be obtained. The CT image $\lambda_{c,odd}(j)$ of odd numbers is shown in FIG. 6, (d), and the CT image $\lambda_{c,even}(j)$ of even numbers is shown in FIG. 6, (e).

Then, in the step 173 shown in FIG. 5, the difference image calculation part 157 of the divided noise measurement part 155 shown in FIG. 4 obtains differences of the CT image $\lambda_{c,odd}(j)$ of odd numbers, and the CT image $\lambda_{c,even}(j)$ of even numbers, as shown by the equation (1), to obtain a difference image $\Delta\lambda_c(j)$.

[Equation 1]

$$\Delta\lambda_c(j)=\lambda_{c,odd}(j)-\lambda_{c,even}(j) \text{ or } \Delta\lambda_c(j)=\lambda_{c,even}(j)-\lambda_{c,odd}(j) \quad (1)$$

FIG. 6, (f) shows an example of the difference image $\Delta\lambda_c(j)$. Since the CT image $\lambda_{c,odd}(j)$ of odd numbers, and the CT image $\lambda_{c,even}(j)$ of even numbers are CT images obtained by reconstruction from 2 sets of data obtained by dividing the measured projection data, they contain images of the same imaging object. Therefore, the difference image $\Delta\lambda_c(j)$ consisting of difference of both images does not contain image of the imaging object as shown in FIG. 6, (f), and thus an image of distribution of CT values of noises contained in the CT images is obtained.

The CT values of the noises shown in the difference image $\Delta\lambda_c(j)$ are values corresponding to the measured projection data obtained after the division. Specifically, the CT values of the noises are values amplified by $\sqrt{2}$ times due to the division of the measured projection data into two sets of data. Therefore, correction is performed in the following step 174 to obtain a corrected difference image $\Delta\lambda'_c(j)$ showing intensity distribution of CT values of noises corresponding to the CT values of the measured projection data not divided.

Specifically, in the step 174 shown in FIG. 5, in order to correct the intensities of the CT values of the noises of the difference image $\Delta\lambda_c(j)$, the difference image $\Delta\lambda_c(j)$ is multiplied by a correction coefficient α to obtain the corrected difference image $\Delta\lambda'_c(j)$ shown in FIG. 6, (g). Since the values are amplified by $\sqrt{2}$ times by the difference calculation processing represented by the equation (1) in the case of division into two sets of data, the correction coefficient a for the correction is defined to be $1/\sqrt{2}$ ($\alpha=\sqrt{2}$). The corrected difference image $\Delta\lambda'_c(j)$ represents information (CT value) only on the noises, obtained by removing information on the imaging object from the CT image reconstructed from the measured projection data not divided.

When the steps 172 and 173 are performed after the data between the channels of the measured projection data $R_{c,odd}(i)$ and $R_{c,even}$ (obtained after the division are interpolated to increase the channel numbers up to the channel number before the division, the aforementioned correction coefficient α is 1 (α=1).

Then, in the step 175 shown in FIG. 5, the divided noise measurement part 155 sets a region of interest in the corrected difference image $\Delta\lambda'_c(j)$, and calculates amplitudes (intensities) of the CT values of the noises in the region of interest. Specifically, the region of interest is set at a predetermined position in the corrected difference image $\Delta\lambda'_c(j)$, and in order to obtain intensities of the noises in the region of interest, variation of the CT values (amplitudes) of the noises of the region of interest are obtained. For example, as index of the variation, a standard deviation σ is calculated. The intensities of the noises of the region of interest (standard deviation σ) can be thereby obtained. The region of interest is defined to be, for example, a region of a length of 100 pixels (x direction) and a width of 100 pixels (y direction) of which center is a pixel j'.

The divided noise measurement part 155 shifts the position of the center pixel j' of the region of interest, calculates intensities (standard deviation σ) of the noises for the region of interest of each position, and correlates the obtained values of the standard deviation σ with a specific position (for example, the center pixel j') of the region of interest to generate a noise image Nc(j) as shown in FIG. 6, (h).

Further, in the step 176 shown in FIG. 5, the added image calculation part 156 shown in FIG. 4 adds the CT image $\lambda_{c,odd}(j)$ of odd numbers and the CT image $\lambda_{c,even}(j)$ of even numbers obtained in the step 172 as represented by the equation (2) to generate an added image $\lambda^{k=0}(j)$ shown in FIG. 6, (i).

[Equation 2]

$$\lambda^{k=0}(j) = \frac{\lambda_{c,odd}(j) + \lambda_{c,even}(j)}{2} \quad (2)$$

The added image $\lambda^{k=0}(j)$ is equivalent to an CT image directly reconstructed from the measured projection data R(i) not divided, and can be used as an initial image of the successive approximation performed by the successive approximation processing part 152. In $\lambda^{k=0}(j)$ in the equation (2), k represents number of times of correction in the successive approximate reconstruction, and k=0 means that $\lambda^{k=0}(j)$ is an initial image.

As described above, by the addition of the divided images performed by the added image calculation part 156, an initial image for the successive approximate reconstruction can be generated. Therefore, calculation time can be shortened compared with the case where the initial image is obtained by performing an image reconstruction processing with the measured projection data R(i) not divided in the analytical reconstruction part 161 described later. When the initial image $\lambda^{k=0}(j)$ is calculated by the analytical reconstruction part 161 described later, it is possible to employ a configuration not comprising the added image calculation part 156. When the added image calculation part 156 is provided, it is possible to employ a configuration not comprising the analytical reconstruction part 161 described later.

Then, the process advances to the step 177 shown in FIG. 5, in which the successive approximation processing part 152 corrects the image by a successive approximate reconstruction processing using the noise intensities calculated by the noise measurement part 155 to generate a CT image in which the noises are highly precisely removed.

Hereafter, the processing of the step 177 will be explained in detail with reference to FIG. 7.

As shown in FIG. 7, the step 177 includes the steps 181 to 188. First, in the step 181, the analytical reconstruction part 161 of the successive approximation processing part 152 (FIG. 4) calculates the CT image $\lambda^{k=0}(j)$ from the measured projection data R(i) corrected by the correction processing part 135 using an analytical reconstruction method such as the known Feldkamp method. When the CT image $\lambda^{k=0}(j)$ is calculated by the added image calculation part 156, the step 181 can be omitted.

Then, as in the step 182, the CT image is successively corrected using the aforementioned CT image $\lambda^{k=0}(j)$ as the initial image in the steps 183 to 186 until the number of times of correction k reaches a number of times K of correction set beforehand.

As the algorithm for the correction of an image, a known successive approximate reconstruction method can be used. Hereafter, use of the SPS (separable paraboloidal surrogate) method will be explained as an example. This SPS is represented by the equation (3).

[Equation 3]

$$\lambda^{k+1}(j) = \lambda^k(j) - \frac{\sum_{i=1}^{I} W(i)C(i,j)\left(R(i) - \sum_{l=1}^{L} C(i,l)\lambda^k(l)\right) + P1}{\sum_{i=1}^{I} W(i)C(i,j)\sum_{l=1}^{L} C(i,l) + P2} \quad (3)$$

In the aforementioned equation (3), W(i) is a weight representing rate of correction of an image. P1 and P2 included in the equation (3) represent equations of the prior calculation of the numerator and the denominator, respectively. According to this embodiment, by introducing noise intensities (standard deviations σ) into P1 and P2 for the prior calculation, the CT image is corrected so that noises are selectively removed. The successive approximate reconstruction according to the equation (3) is performed by the following steps 183 to 186.

First, in the step 183, the forward projection part 162 (FIG. 4) performs calculation of the equation (4) to perform a forward projection processing of the pixels of a CT image $\lambda^k(j)$, and obtain calculated projection data.

[Equation 4]

$$\sum_{l=1}^{L} C(i,l)\lambda^k(l) \quad (4)$$

In the equation (4), l represents number of L of pixels on a line connecting a pixel j to be corrected and an X-ray detector i. C(i,l) represents a ratio of contribution of a pixel l in the X-ray detector i, and as the value of C(i,l), a value varying depending on the position of the X-ray detector, or the method of forward projection calculation or back projection calculation is set.

Then, in the step 184, a difference calculation part 163 (FIG. 4) subtracts the calculated projection data obtained according to the equation (4) from the measured projection data R(i) as represented by the equation (5) to obtain corrected projection data $\Delta R^k(i)$.

[Equation 5]

$$\Delta R^k(i) = R(i) - \sum_{l=1}^{L} C(i,l)\lambda^k(l) \quad (5)$$

Then, in the step 185, the back projection processing part 164 (FIG. 4) performs a back projection processing for the corrected projection data $\Delta R^k(i)$ in accordance with the equation (6) to generate a corrected image $\Delta\lambda^k(j)$.

[Equation 6]

$$\Delta\lambda^k(j) = \frac{\sum_{i=1}^{I} W(i)C(i,j)\Delta R^k(i) + P1}{\sum_{i=1}^{I} W(i)C(i,j)\sum_{l=1}^{L} C(i,l) + P2} \quad (6)$$

As P1 and P2 included in the equation (6), values obtained by the prior calculation part 165 (FIG. 4) in accordance with the equations (7) and (8) are used. The equations (7) and (8) are examples of the equations for obtaining P1 and P2, P1 is obtained by calculation of a first order derivative of the equation (7), and P2 is obtained by calculation of a second order derivative of the equation (8) according to a kind of the prior calculation, the Generalized Geman prior.

[Equation 7]

$$P1 = \beta \sum_{m \in N_j} d_{jm} \psi(\lambda_j^k - \lambda_m^k) \quad (7)$$

[Equation 8]

$$P2 = \beta \sum_{m \in N_j} d_{jm} \frac{\psi(\lambda_j^k - \lambda_m^k)}{\lambda_j^k - \lambda_m^k} \quad (8)$$

In the aforementioned equations (7) and (8), β is a constant representing intensity of prior. $\psi(\lambda_j^k - \lambda_m^k)$ is a function of the difference value $(\lambda_j^k - \lambda_m^k)$ of CT values of 2 pixels in the CT image $\lambda^k(j)$ as a variable, and is represented by the equation (9). $\psi(\lambda_j^k - \lambda_m^k)$ represents correction amount of the CT value (pixel value) of the j-th pixel of the CT image in the prior calculation for the successive approximate reconstruction. $\lambda_j^k$ is a pixel value of the j-th pixel, and $\lambda_m^k$ is a pixel value of the m-th pixel. The m-th pixel is a pixel existing in a predetermined positional relationship with respect to the j-th pixel (for example, relationship, that the m-th pixel is adjacent to the j-th pixel on right or left of the j-th pixel, or above or below the j-th pixel). The number of the m-th pixel is a predetermined number not smaller than 1 (for example, 8). As seen from the equation (7) and (8), when the number of the m-th pixel is 2 or larger, the total of $\psi(\lambda_j^k - \lambda_m^k)$ (Σ) for every m-th pixel is obtained, and used for P1 and P2.

[Equation 9]

$$\psi(\lambda_j^k - \lambda_m^k) = \frac{\delta^p(\lambda_j^k - \lambda_m^k)\left\{(\lambda_j^k - \lambda_m^k)^2\left(1 - \frac{p}{2}\right) + \delta^2\right\}}{\left\{(\lambda_j^k - \lambda_m^k)^2 + \delta^2\right\}^{\left(\frac{p}{2}+1\right)}} \quad (9)$$

The symbols p and δ included in the equation (9) represent parameter constants used for the prior calculation.

Figure 8:
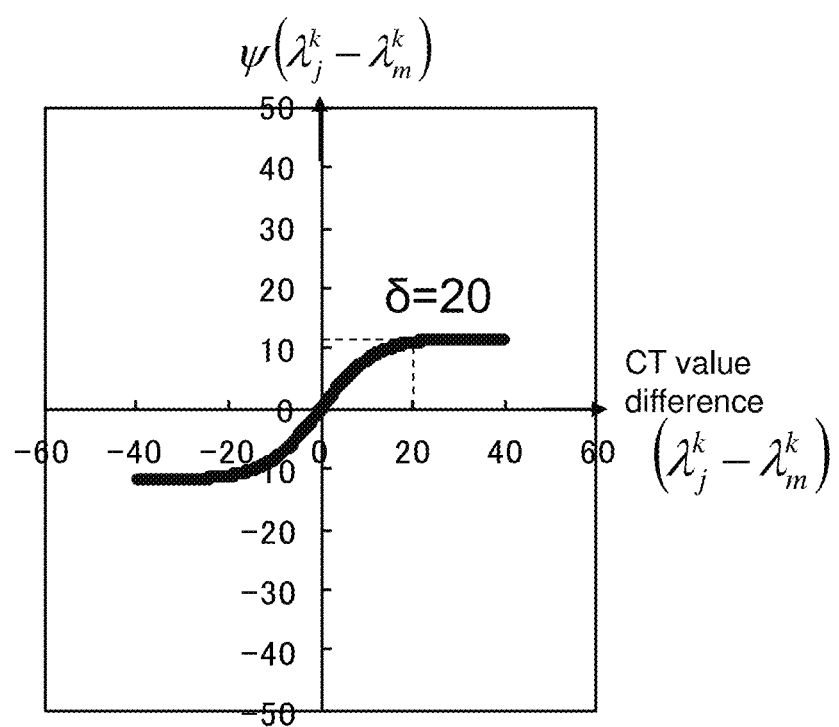
FIG. 8 is a graph showing an example of the function used for the prior calculation according to the embodiment 1.

According to the present invention, correction amount of the CT value of the j-th pixel used in the prior calculation is changed according to the magnitude relation between the CT value difference of the j-th pixel and the m-th pixel, and the noise intensity σ (hereafter referred to as $\sigma_j$) obtained for the region of interest of which center pixel is the j-th pixel. Specifically, for example, as $\psi(\lambda_j^k - \lambda_m^k)$ representing the correction amount of the CT value (pixel value) of the j-th pixel, such a function as that of the equation (9) is used, and the constant δ in the equation (9) is made to correspond to the noise intensity (standard deviation $\sigma_j$), so that δ is equal to $\sigma_j$ (δ=$\sigma_j$). FIG. 8 shows a graph of $\psi(\lambda_j^k - \lambda_m^k)$ of the equation (9). In FIG. 8, the horizontal axis indicates the difference of CT values of 2 pixels $(\lambda_j^k - \lambda_m^k)$ and the vertical axis indicates the value of $\psi(\lambda_j^k - \lambda_m^k)$ of the equation (9). When the absolute value of the CT value difference $|(\lambda_j^k - \lambda_m^k)|$ is smaller than δ, $\psi(\lambda_j^k - \lambda_m^k)$ becomes larger with increase of the CT value difference $(\lambda_j^k-\lambda_m^k)$, but when the absolute value of the CT value difference $|(\lambda_j^k-\lambda_m^k)|$ is larger than $\delta$, $\psi(\lambda_j^k-\lambda_m^k)$ has a constant value. FIG. 8 shows a graph for $\delta$=20 as an example. It is also possible to use two or more constants ($\delta$1, $\delta$2, etc.) as the constant $\delta$, and determine the correction amount of the CT value $\psi(\lambda_j^k-\lambda_m^k)$ according to the magnitude relation of the CT value difference $(\lambda_j^k-\lambda_m^k)$ and $\delta$1, $\delta$2, etc.

As described above, by using $\psi(\lambda_j^k-\lambda_m^k)$ of the equation (9), when the absolute value of the CT value difference $|(\lambda_j^k-\lambda_m^k)|$ is not larger than the noise intensity $\sigma_j$ (=$\delta$), the CT value of pixel j is corrected according to the CT value difference $(\lambda_j^k-\lambda_m^k)$, whereas when the absolute value of the CT value difference $|(\lambda_j^k-\lambda_m^k)|$ is larger than the noise intensity $\delta_j$ (=$\delta$), the correction amount does not become larger beyond a fixed value, even when the CT value difference becomes larger, and thus the correction amount is suppressed. Therefore, when the CT value of the pixel j is that of a noise (that is, smaller than noise intensity), it can be selectively corrected. On the other hand, when the CT value of the pixel j is that of the image of imaging object (that is, larger than noise intensity), degradation of the CT image by the prior calculation can be prevented.

By the above procedure, a corrected image $\Delta\lambda^k(j)$ of the equation (6) is calculated (step 185).

Then, in the step 186, the image correction part 166 performs calculation of the equation (10) to obtain a CT image $\lambda^{k+1}(j)$ corrected by using the corrected image $\delta\lambda^k(j)$.

[Equation 10]

$$\lambda^{k+1}(j)=\lambda^k(j)-\Delta\lambda^k(j) \quad (10)$$

After completing the aforementioned steps 183 to 186, in the step 187, the number of times k of the correction is incremented to k+1, and the process returns to the step 182. By this procedure, the steps 182 to 187 are repeatedly performed until the incremented number of times k of the correction becomes equal to the number of times K of the correction set beforehand. When the number of times k of the correction reaches K, the correction is ended, the process advances to the step 188, and a CT image is outputted, and displayed on the monitor 123 by the image display part 137 (FIG. 2).

Since this CT image is generated by the successive approximate reconstruction, the calculated projection data obtained by projecting that CT image well agree with the measured projection data, and thus a CT image highly precisely reconstructed from the measured projection data can be obtained.

In the step 188, it is also possible to transmit the CT image to an external terminal through a network such as local area network, telephone line, and the Internet using a network adaptor.

Further, in this embodiment, the noise intensity is measured from a CT image in advance, and correction amount of a CT value of a pixel is changed according to magnitude relation between a CT value of a pixel in a region of interest, and noise intensity through the steps 171 to 177 and the steps 181 to 188, and therefore noise can be reduced with suppressing degradation of image of imaging object.

In this embodiment, the equation (9) is defined so that when the absolute value of the CT value difference $|(\lambda_j^k-\lambda_m^k)|$ is larger than the noise intensity $\sigma_j$(=$\delta$), $\psi(\lambda_j^k-\lambda_m^k)$ becomes constant. However, the present invention is not limited to such a configuration, and there may be used a configuration that when $|(\lambda_j^k-\lambda_m^k)|$ is larger than the noise intensity $\sigma_j$ (=$\delta$), the value of $\psi(\lambda_j^k-\lambda_m^k)$ becomes smaller than that of the case where $|(\lambda_j^k-\lambda_m^k)|$ is smaller than $\sigma_j$.

In this embodiment, it is focused on that the noise reduction effect of the successive approximate reconstruction depends on precision of the measured projection data, and preset values of parameters, and measured noise intensity is used as a value of parameter for successive approximate reconstruction. Therefore, the measured noise intensity can be easily introduced into the processing without significantly changing the successive approximate reconstruction processing itself.

In this embodiment, $\delta$ is chosen as a parameter for introducing the measured noise intensity, but the present invention is not limited to such a configuration, and can be applied to other parameters used for the prior calculation.

In this embodiment, a plurality of regions of interest are set with shifting the positions thereof over the whole region of the CT image, the noise intensity (standard deviation $\sigma$) for the whole region of CT image is thereby obtained (step 175 shown in FIG. 5), and the prior calculation is performed with introducing noise intensity for the whole CT image. However, according to the present invention, noise intensity may not necessarily be obtained for the whole region of CT image, and noise intensity may be measured for one or more regions of interest. In such a case, in the processing of the successive approximate reconstruction (step 177 shown in FIG. 5), the measured noise intensity is introduced only into the parameter for the prior calculation for the region of interest of the CT image, and predetermined values are used for the parameters of the prior calculation for regions other than the region of interest. With such a configuration, noise can be selectively removed at least for the region of interest, and degradation of the image of the imaging object can be suppressed.

The successive approximate reconstruction procedure represented by the aforementioned equation (3) is an example, and the present invention may be applied to any of other methods such as known OS-SPS, PWLS, OS-PWLS, ASIRT, MSIRT, GRADY, CONGR, ART, SART, ML-EM, OS-EM, FIRA, RAMLA, and DRAMA.

There may also be employed a configuration that the difference image $\Delta\lambda_c(j)$, corrected difference image $\Delta\lambda'_c(j)$, noise image $N_c(j)$, and added image $\lambda^{k=0}(j)$ shown in FIGS. 6, (*f*) to (*i*) are displayed on the monitor 123 of the image generation part 103 for the operator etc.

In the above explanation of this embodiment, the CT image is reconstructed by using the measured projection data obtained from one rotation, but the present invention is not limited to such a configuration using measured projection data for one rotation, and can be applied to the known half reconstruction or reconstruction using measured projection data for more than one rotation.

In the above explanation of this embodiment, an example is explained where the measured projection data are obtained by the conventional scanning method in which the bed 5 and the gantry 3 are in a stationary state. However, the present invention is not limited to such a configuration, and of course can also be applied to measured projection data obtained by the step and shoot method in which the conventional scan is performed with repeatedly moving and stopping the bed 5 with constant intervals, or the helical scan method in which scan is performed with moving the bed 5.

In the above explanation of this embodiment, an X-ray CT apparatus for living bodies is shown as an example, but the present invention can of course be applied to an X-ray CT apparatus for nondestructive tests such as those for explosive substance test and product inspection. In the above explanation of this embodiment, a known multi-slice X-ray CT apparatus of the third generation is explained as an example, but the present invention can also be applied to the known first, second, and fourth generation X-ray CT apparatuses, and can also be applied to known single slice X-ray CT apparatuses or electron beam CT apparatuses.

In the above explanation of this embodiment, there is explained an example in which the direction for the division of the measured projection data is set to be the channel direction or the slice direction as shown in FIG. 3. However, the direction for the division may be set to be the projection angle direction. When the direction for the division is set to be the projection angle direction, artifacts are more easily generated in regions remote from the center of the divided CT image (peripheral part). Since these artifacts remain in the difference image obtained after the difference calculation processing and the corrected difference image, errors in the measurement of noise intensity become larger in peripheral parts.

<Embodiment 2>

Hereafter, the X-ray CT apparatus of the embodiment 2 will be explained.

The embodiment 1 explained above employs a configuration that the measured projection data are divided, CT images are generated from the sets of the divided measured projection data, respectively, and a difference image is obtained from them. In contrast, in the embodiment 2, difference of the divided measured projection data is obtained first, and a difference image is reconstructed from the measured projection data as the difference.

Hereafter, the configuration of the X-ray CT apparatus of the embodiment 2 will be explained mainly for the parts of the configuration different from those of the X-ray CT apparatus of the embodiment 1. In the following explanation, the same numerals are attached to the same parts of the configuration as those of the embodiment 1, and detailed explanations thereof are omitted.

Figure 9:
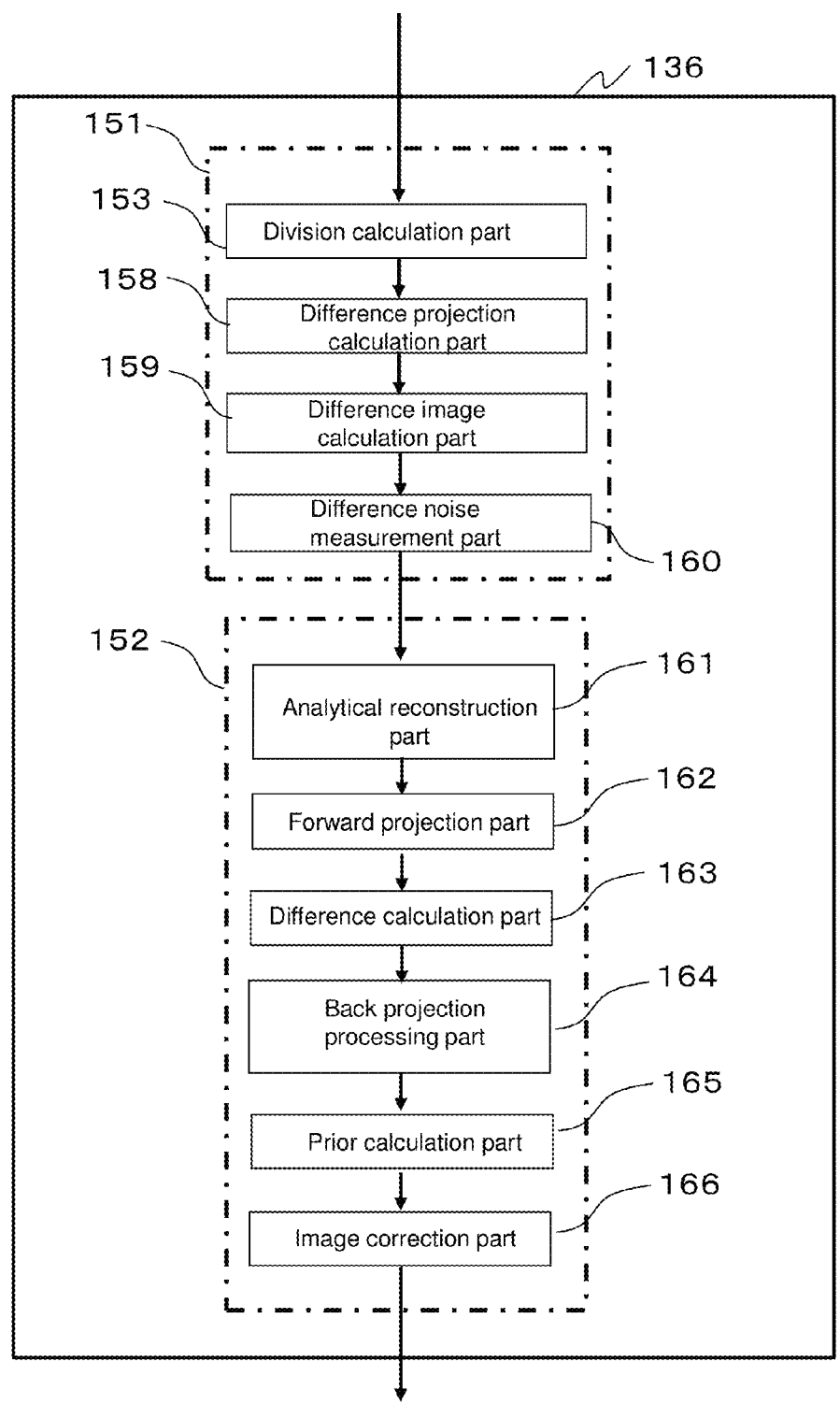
FIG. 9 is a functional block diagram for explaining the function of the successive approximate reconstruction part 136 according to the embodiment 2.

The detailed functional configuration of the successive approximate reconstruction part 136 of the embodiment 2 is shown in FIG. 9. The successive approximate reconstruction part 136 comprises the noise measurement part 151 that measures noise of a CT image, and the successive approximation processing part 152 that introduces the measured noise and successively corrects the CT image. The noise measurement part 151 comprises the division calculation part 153 that divides measured projection data, a difference projection calculation part 158 that calculates difference value of two or more kinds of the divided measured projection data, a difference image calculation part 159 that calculates a difference image by reconstructing the calculated difference measured projection data, and a difference noise measurement part 160 that measures noise from the obtained difference image.

The division calculation part 153 divides measured projection data in the same manner as that used by the division calculation part 153 of the embodiment 1 shown in FIG. 4. An interpolation processing may be or may not be performed for the divided measured projection data as described for the embodiment 1.

The difference projection calculation part 158 obtains difference of the divided measured projection data. Then, the difference image calculation part 159 reconstructs an image from the difference of the measured projection data using an analytical reconstruction method such as the known Feldkamp method to obtain a difference image $\Delta\lambda_c(j)$ shown in FIG. 6, (f).

Then, the difference noise measurement part 160 multiplies the difference image $\Delta\lambda_c(j)$ by a correction coefficient a in order to correct the value of the obtained difference image $\Delta\lambda_c(j)$ for the noise intensity of the CT image in the same manner as that of the step 174 shown in FIG. 5. The result of the multiplication is referred to as a corrected difference image $\Delta\lambda'_c(j)$ shown in FIG. 6, (g). For example, when any interpolation processing is not performed for the divided measured projection data, the correction coefficient $\alpha=1/\sqrt{2}$ is multiplied in order to correct the noise intensity amplified $\sqrt{2}$ times by the difference calculation processing performed by the difference projection calculation part 158. The corrected difference image $\Delta\lambda'_c(j)$ represents information (CT value) of only the noise obtained by removing information on the imaging object (CT value) from the CT image. When an interpolation processing is performed for the divided measured projection data, the aforementioned correction coefficient α is of course changed according to the processing method.

Then, the difference noise measurement part 160 sets a region of interest in the corrected difference image $\Delta\lambda'_c(j)$, and obtains the standard deviation σ for the region of interest to obtain intensity of the noise in the same manner as that used in the step 175 shown in FIG. 5, in order to obtain a noise image that represents noise distribution. The difference noise measurement part 160 further shifts the position of the center pixel j' of the region of interest, and calculates intensities (standard deviation σ) of the noises for the region of interest at each position, and correlates the obtained values of the standard deviation σ with the center pixel j' to generate a noise image $N_c(j)$ as shown in FIG. 6, (h).

The operation of the successive approximation processing part 152 is the same as that explained for the embodiment 1, and therefore explanation thereof is omitted.

According to the embodiment 2, the difference between the divided measured projection data is obtained, and used to reconstruct a difference image. Therefore, the number of image to be reconstructed is fewer than that of the processing of reconstructing images from each of the sets of the divided measured projection data, and obtaining difference of the images to obtain a difference image as in the embodiment 1, and therefore there are obtained effects that the calculation time can be shortened, and the required capacity of the memory can be reduced. These effects of shortening the calculation time, and reducing the required capacity of the memory are especially markedly obtained when the number of the sets of the divided measured projection data is large.

<Embodiment 3>

Hereafter, the X-ray CT apparatus of the embodiment 3 will be explained.

The embodiment 1 employs a configuration that the division calculation part 153 divides the measured projection data for a predetermined direction for division chosen by the operator on the noise measurement setting region 144 shown in FIG. 3, irrespective of the position of the region of interest on the CT image. In contrast, according to the embodiment 3, the noise measurement part 151 chooses the direction for the division of the measured projection data performed by the division calculation part according to the position of the region of interest on the CT image.

For example, there is employed a configuration that the division calculation part 153 can divide the measured projection data for at least two directions among the channel direction, slice direction, and projection angle direction. The noise measurement part 151 is constituted so that when the region of interest locates in a predetermined area with respect to the position of CT image corresponding to the rotation center of the rotation plate, the noise measurement part 151 chooses the projection angle direction as the direction for the division of the measured projection data, and when the region of interest locates outside the predetermined area, it chooses the channel direction or the slice direction as the direction for the division.

By choosing the direction for the division according to the position of the region of interest on the CT image as described above, accuracy of the measurement of noise intensity can be enhanced.

First, the reason why artifacts are generated in peripheral parts of a CT image due to division for the projection angle direction will be explained. For example, if measured projection data obtained by 900 times of imaging per one rotation are equally divided into two sets for the projection angle direction, each of the CT images obtained from the divided measured projection data is equivalent to an image reconstructed from measured projection data obtained by 900/2=450 times [time/rotation] of imaging. If the number of times of imaging per rotation decreases, the sampling density for the projection angle direction becomes smaller, and therefore more artifacts are generated at positions of a larger distance r from the rotation center. For example, FIG. 10, (a) shows an example of the corrected difference image calculated from the measured projection data divided for the projection angle direction. Since the number of times of imaging (number of data acquisition) per rotation is small, artifacts of strong intensity are generated in a region 192 outside a line 191 shown in FIG. 10, (a) as a border. These artifacts correspond to errors generated by the division of the measured projection data for the projection angle direction, and when the region of interest locates in a peripheral part of the CT image, the noise intensity measurement error becomes large.

Figure 10:
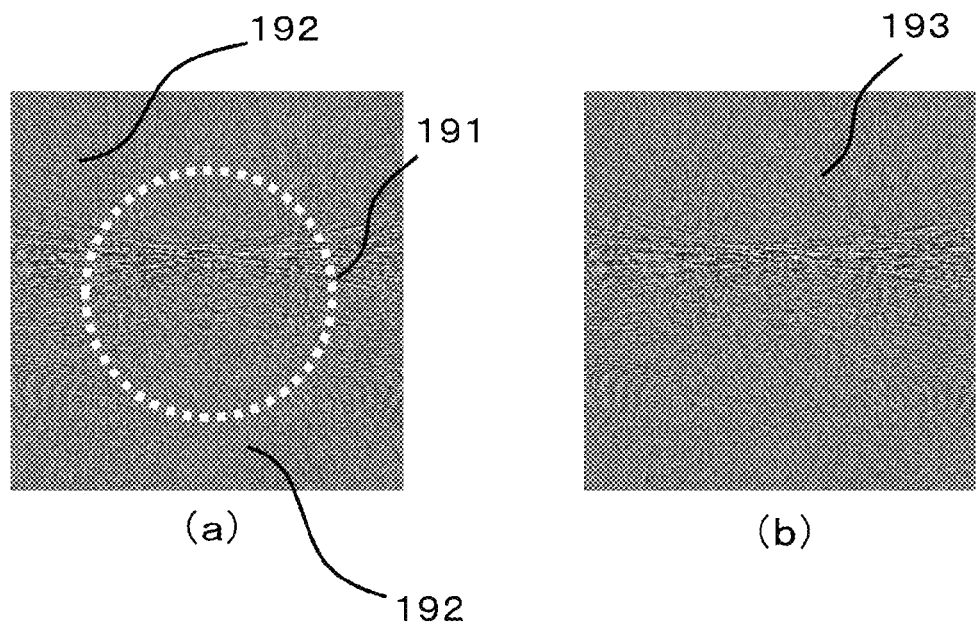
FIG. 10 includes explanatory drawings showing corrected difference images calculated from the measured projection data divided for (a) projection angle direction, or (b) channel direction, and regions thereof according to the embodiment 3.

On the other hand, if the measured projection data (1000 channels) are equally divided into two sets for the channel direction, the CT image is reconstructed with the measured projection data of 1000/2=500 channels. The CT image must be reconstructed with no data between the 500 channels (with data of 500 channels), or with data for 1000 channels, which is increased by interpolation calculation, and artifacts are uniformly generated over the reconstructed CT image irrespective of the position. Therefore, noise intensity measurement errors are uniformly generated over the entire region 193 of the corrected difference image irrespective of the position of the region of interest on the CT image, as shown in FIG. 10, (b).

Therefore, according to the embodiment 3, the CT image is divided into regions, and a direction for the division defined beforehand that makes noise intensity measurement error small is chosen for each region. A direction for the division that makes measurement error of noise intensity small is chosen depending on in which region the position locates. Specifically, when the number of times of imaging per rotation is a usual number of times of imaging, in a center region 195 within a predetermined distance (for example, r=200 mm) from the center of the CT image (position corresponding to the rotation center of the rotation plate 4), division of the measured projection data for the projection angle direction provides smaller measurement error of noise intensity as in the noise image shown in FIG. 11, and therefore the projection angle direction is chosen. In an outer region 196 remote from the center of the CT image by a distance longer than the predetermined distance, division of the measured projection data for the channel direction or slice direction provides smaller measurement error of noise intensity compared with that provided by division of the measured projection data for the projection angle direction, and therefore the channel direction or slice direction is chosen. As the radius r of the line 194 as the border of the central region 195 and the outer region 196, a predetermined value may be used, or a value inputted by the operator from the imaging condition input part 131 may be used.

Figure 11:
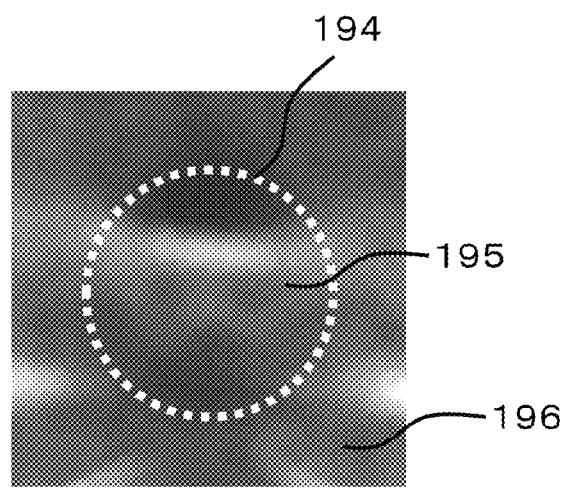
FIG. 11 is an explanatory drawing showing a noise image in which the projection angle direction or the channel direction is selected for each region of the CT image according to the embodiment 3.

Specific processing method is as follows. For example, through the steps 171 to 176 of the embodiment 1, the noise measurement part 151 divides the measured projection data for the channel direction, and generates a noise image $N_c(j)$, and at the same time, the noise measurement part 151 divides the measured projection data for the projection angle direction, and generates a noise image $N_p(j)$. By using the pixel values of the noise image $N_p(j)$ for the center region 195, and the pixel values of the noise image $N_c(j)$ for the outer region 196, a noise image provided through the selection can be generated as shown in FIG. 11.

In the aforementioned explanation, one of the channel direction and the slice direction is chosen as the direction for the division for each of the central region 195 and the outer region 196. However, the present invention is not limited to such a method of performing the division for only one direction, and may use a configuration that there are used noise intensities obtained by weighting those obtained for two or more directions for the division, and adding them. That is, the noise measurement part 151 chooses at least two directions from the channel direction, slice direction, and projection angle direction as the direction for the division of the measured projection data performed by the division calculation part 153, obtains noise intensities for the directions, performs weighting of the noise intensities, obtains sum of the weighted noise intensities, and uses the sum as the noise intensity. In this procedure, the value of each weight is changed according to the position of the region of interest on the CT image. By this procedure, the measurement error of the noise intensity can be made small according to the position of the region of interest on the CT image.

Specifically, the noise measurement part 151 first divides the measured projection data for the channel direction, and generates a noise image $N_c(j)$, and at the same time, the noise measurement part 151 divides the measured projection data for the projection angle direction, and generates a noise image $N_p(j)$, through the steps 171 to 176 of the embodiment 1.

As shown by the equation (11), the pixel values of the noise image $N_c(j)$ and $N_p(j)$ are multiplied by weighting functions $w_c(r)$ and $w_p(r)$, of which variable is the distance r from the rotation center, respectively, and the products are added to obtain an added noise image $N_{total}(j)$.

[Equation 11]

$$N_{total}(j) = N_c(j) \cdot w_c(r) + N_p(j) \cdot w_p(r) \text{ provided that} \quad (11)$$
$$w_c(r) + w_p(r) = 1$$

The weighting functions $w_c(r)$ and $w_p(r)$ mentioned above are appropriately chosen according to the imaging part set on the imaging part setting region 145 shown in FIG. 3. The weighting functions for the two direction are defined so that, for example, the condition that $w_c(r)+w_p(r)=1$ is satisfied. By such a definition, the noise values measured for two or more directions can be changed continuously.

For example, in imaging of a head region, because of small FOV, high accuracy is desired for a region near the rotation center. Therefore, a noise image $N_p(r)$ for the projection angle direction is used for the whole region. In such a case, if $w_c(r)$ is set to be 0 ($w_c(r)=0$), the noise measurement for the channel direction can be omitted, and therefore calculation time can be shortened. On the other hand, in imaging of an abdominal region, because of large FOV, high accuracy is desired also for a peripheral region. Therefore, the weighting functions are set so that, for the region where r is not smaller than 200 mm, the weighting function $w_p(r)$ for the projection angle direction becomes larger than the weighting function $w_c(r)$ for the channel direction.

The weighting functions may also be set according to the number of times of imaging per rotation. For example, when the number of times of imaging per rotation is large (for example, 2000 [times/rotation]), the sampling density for the projection angle direction becomes high in peripheral regions, and therefore the measurement error of the noise image for the projection angle direction becomes small not only in the center region 195, but also in the outer region 196. In such a case, if $w_c(r)$ is set to be 0 ($w_c(r)=0$), noise measurement for the channel direction can be omitted, and therefore calculation time can be shortened. On the other hand, when the number of times of imaging per rotation is small (for example, 1000 [times/rotation]), the sampling density for the projection angle direction becomes low in peripheral regions of the CT image. Therefore, the measurement accuracy of the noise image measured from the measured projection data for the projection angle direction is reduced in the peripheral regions. Therefore, in order to improve the measurement accuracy, weighting functions are set so that that the weighting function $w_p(r)$ for the projection angle direction becomes smaller than the weighting function $w_c(r)$ for the channel direction for the outer region 196 (for example, r=200 mm or longer).

In addition, the directions for the division are not limited to two directions of the channel direction and projection angle direction, and can be chosen as an arbitrary combination of two or more of the channel direction, slice direction, and projection angle direction.

As the noise image used in this embodiment 3, not only that obtained by the processing method of the embodiment 1, but also the noise image obtained by the processing method of the embodiment 2 can of course be used.

In this embodiment 3, the noise image obtained with the directions for the division different for every region as shown in FIG. 11 can be displayed on the monitor 123 of the image generation part 103.

Since the other parts of the configuration are the same as those of the embodiments 1 and 2, explanations are omitted.

<Embodiment 4>

Hereafter, the X-ray CT apparatus of the embodiment 4 will be explained.

As the embodiment 4, there is explained a case where a fan beam/parallel beam conversion is introduced into the noise intensity measurement processing performed by the functions of the division calculation part 153, the divided image calculation part 154, and the divided noise measurement part 155 according to the embodiment 1 shown in FIG. 4.

Figure 12:
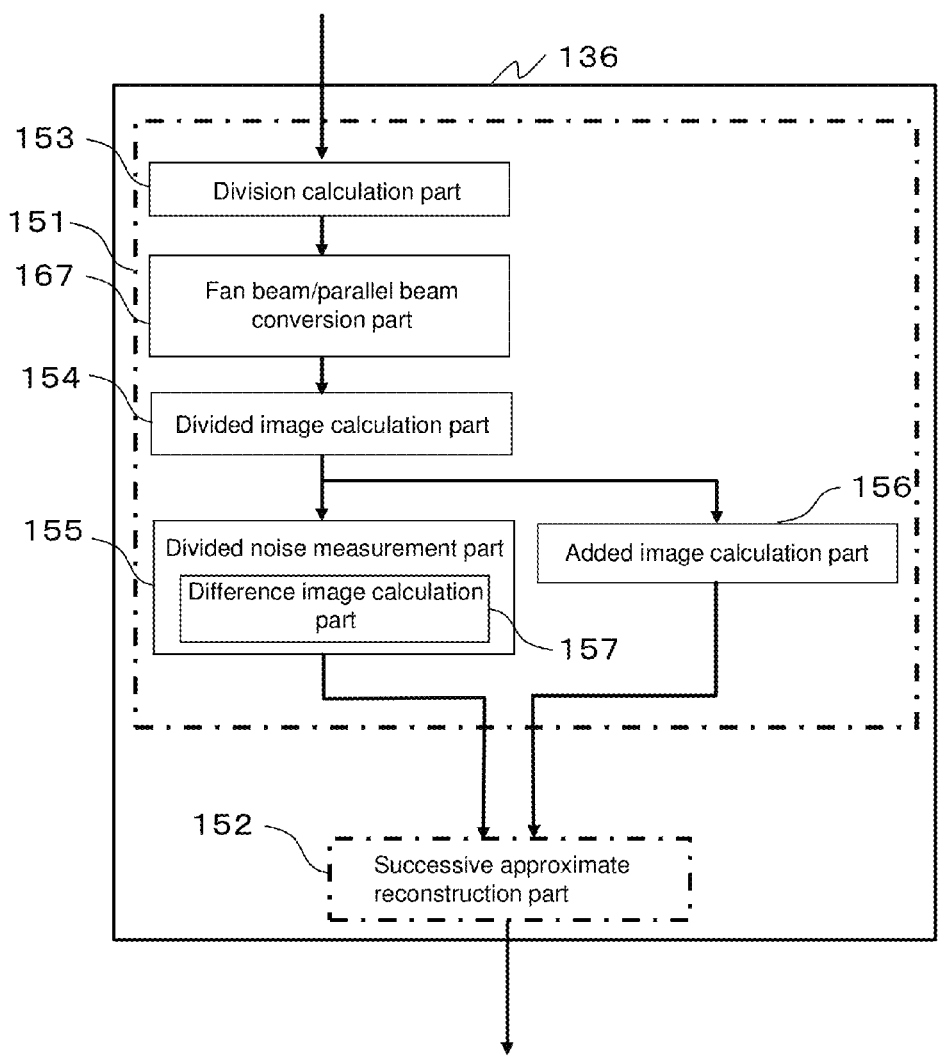
FIG. 12 is a functional block diagram for explaining the function of the successive approximate reconstruction part 136 according to the embodiment 4.

According to the embodiment 4, the X-ray tube 1 irradiates X-rays in the shape of fan (fan beam) on the X-ray detector 2. The configuration of the successive approximate reconstruction part 136 is shown in FIG. 12. As shown in FIG. 12, a fan beam/parallel beam conversion part 167 is disposed between the division calculation part 153 and the divided image calculation part 154, and the divided measured projection data (fan beam data) are converted into parallel beam data. As the conversion method, a known method is used. The divided image calculation part 154 generates CT images from the converted measured projection data (parallel beam data), respectively, and the divided noise measurement part 155 and the difference image calculation part 157 measure noise intensity of the CT images.

As described above, in this embodiment 4, the fan beam/parallel beam conversion of the divided measured projection data is performed, and noise intensity can be thereby measured with high precision using the measured projection data undergone the fan beam/parallel beam conversion. This is because, if the fan beam/parallel beam conversion of the measured projection data is carried out before the division by the division calculation part 153, correlation of the noises of the divided measured projection data becomes high, highly correlated noises are compensated by the difference calculation processing performed by the difference image calculation part 157, and therefore the noises can no longer be detected with sufficient accuracy. For example, if the measured projection data before the conversion at projection angles θ-1, θ-2, . . . are represented as measured projection data $R_{fan}(1,θ-1)$, $R_{fan}(1,θ-2)$, . . . , by interpolation processing of these, the measured projection data $R_{para}(i,θ)$ at the projection angle θ after the conversion into parallel beam are calculated. If these data are divided, the divided measured projection data $R_{para,odd}(i,θ)$ and $R_{para,even}(i,θ)$ include data calculated from the same measured projection data $R_{fan}(i,θ-1)$, $R_{fan}(i,θ-2)$, . . . , correlation of the noises becomes high. Therefore, when the difference image calculation part 157 obtains difference, highly correlating noises are compensated, and the measurement accuracy of noise is reduced. On the other hand, as in the embodiment 4, if the measured projection data are divided as fan beam data, and subjected to the fan beam/parallel beam conversion after the division, correlation of the noises in the divided measured projection data does not become high.

As described above, by performing processings in the division calculation part 153, the fan beam/parallel beam conversion part 167, and the divided image calculation part 154 in this order, as shown in FIG. 12, fan beam/parallel beam conversion can be realized with preventing reduction of the noise measurement accuracy.

Since the other parts of the configuration are the same as those of the embodiment 1, explanations thereof are omitted.

In addition, it is also possible to apply the configuration of the embodiment 2 to this embodiment 4. In such a case, by disposing the, fan beam/parallel beam conversion part 167 between the division calculation part 153, and the difference projection calculation part 158 shown in FIG. 9 for the embodiment 2, the fan beam/parallel beam conversion can be realized with preventing reduction of accuracy of the noise measurement as explained above.

<Embodiment 5>

Hereafter, the X-ray CT apparatus of the embodiment 5 will be explained.

The embodiment 1 employs a configuration that the divided noise measurement part 155 obtains noise intensities (standard deviation σ of CT values) for a region of interest of a predetermined size (for example, 100 pixels×100 pixels with the center at pixel j') set in the corrected difference image $Δλ'_c(j)$. Therefore, if an image of a tissue showing a significantly different noise intensity level (for example, bone, air, etc.) is contained in the region of interest, the measurement accuracy may be reduced. Therefore, in this embodiment 5, the region of interest is set to have a shape corresponding to the shape of tissue of the imaging object.

Specifically, in the embodiment 5, the shape of the region of interest to be set in the corrected difference image is optimized by using information of the CT image, so that it corresponds to the shape of tissue of the imaging object, as shown in FIG. 13. Presence of a tissue showing markedly different level of noise intensity in the region of interest can be thereby prevented. As the CT image used for the optimization of the shape of the region of interest, a divided image generated by the divided image calculation part 154, or a CT image calculated by the added image calculation part 156 or the analytical reconstruction part 161 is used. For example, it is assumed that a region in which distribution of the CT values of the CT image is uniform is a tissue not showing a noise intensity of high level, and the shape of the region of interest is set on the basis of such an assumption. Whether distribution of CT values is uniform or not is judged on the basis of whether variation of the CT values is within a predetermined range or not. For example, if a region of interest 201 in the liver shown in FIG. 13, (a) is set to be a circle of a predetermined area, the CT value distribution in the region of interest 201 is uniform. Therefore, the region of interest 201 of the same shape is set at the same position in the difference image shown in FIG. 13, (b), and the noise intensity (standard deviation o of CT values) of the region of interest 201 is obtained. In contrast, as shown in FIG. 13, (a), if a region of interest 202 around the spinal cord is set to be a circle, it includes a part of the spinal cord, and since the level of the CT values of the spinal cord is higher than the level of the CT values of the parts around the spinal cord, the CT value distribution is not included in the predetermined range. Therefore, the shape of the region of interest 202 is changed so that the spinal cord is excluded (optimization). This optimized region of interest 202 is set at the same position in the difference image shown in FIG. 13, (b), and the noise intensity of the region of interest 202 is obtained.

The processing for changing the shape of the region of interest 202 so that the region showing a different level of CT values is excluded from the region of interest 202 can be realized by the noise measurement part 151 through judging level of CT value for every pixel in the region of interest 202, and excluding pixels of different level. There can also be employed a configuration that the CT image shown in FIG. 13, (a) is displayed on a monitor, and the operator can change the shape of the region of interest 202 by using the mouse 112, or the like. In such a case, the operator needs to determine a tissue in which CT values and noise intensities of adjacent pixels are at a similar level, and select the region of interest.

According to the configuration of the embodiment 5, a tissue showing a significantly different noise intensity level (for example, bone, air, etc.) does not exist in the region of interest, and therefore the measurement accuracy of the noise intensity of the region of interest can be improved.

Since the other parts of the configuration are the same as those of the embodiment 1, explanations thereof are omitted.

<Embodiment 6>

In the embodiment 1, in order to use the measured noise intensity ($\sigma$) for the prior calculation, $\sigma$ is used to substitute for the parameter $\delta$ in the equation (9) ($\delta=\sigma$). In contrast, in the embodiment 6, a value obtained by multiplying $\sigma$ by a contribution ratio q is used to substitute for $\delta$ as shown in the equation (12). With such a configuration, the level of noise desired to be reduced can be chosen by arbitrarily setting the contribution ratio q.

[Equation 12]

$$\delta = \sigma \cdot q \quad (12)$$

Figure 14:
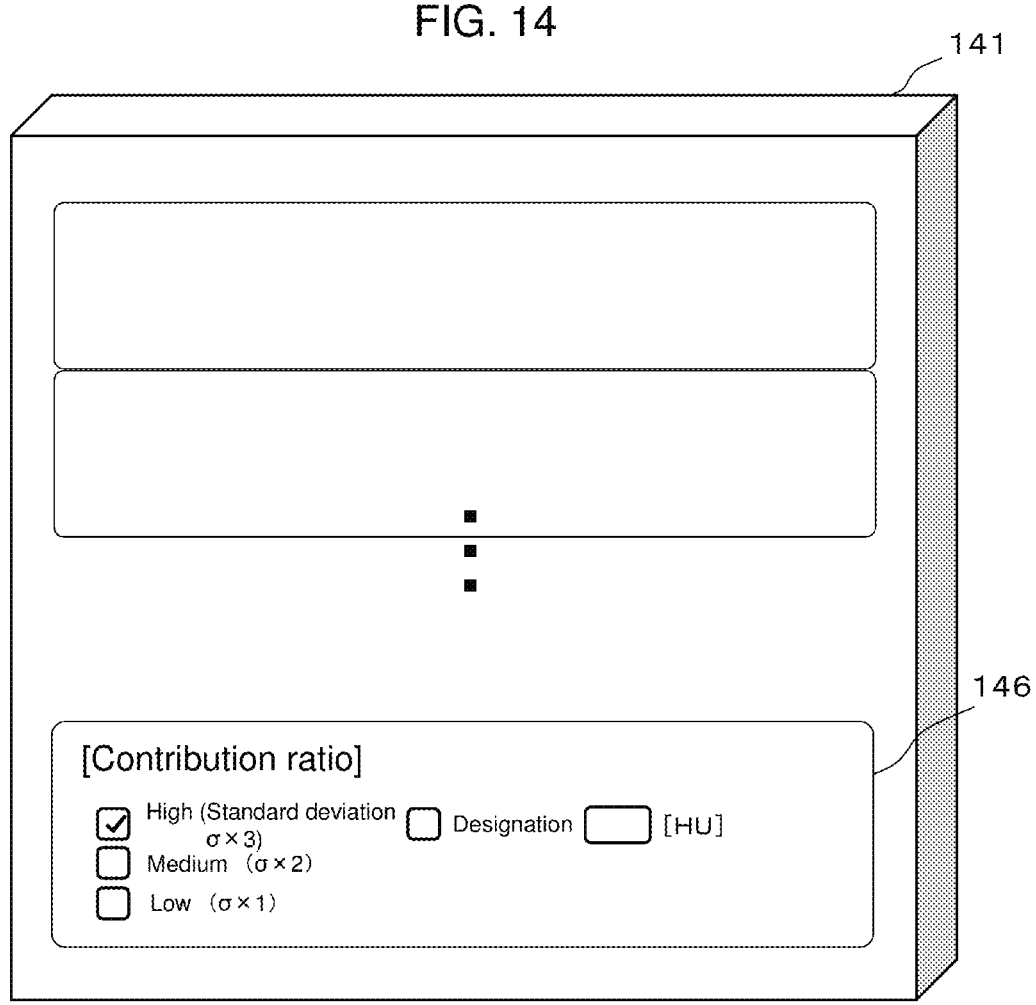
FIG. 14 is an explanatory drawing for explaining a contribution ratio setting region on an input screen according to the embodiment 6.

The imaging condition reception screen 141 of the embodiment 6 is shown in FIG. 14. The imaging condition receptionist screen 141 shown in FIG. 14 has a configuration that a contribution ratio setting region 146 for setting the contribution ratio is added to the imaging condition reception screen 141 shown in FIG. 3.

The operator chooses intensity of noises desired to be reduced on the contribution ratio setting region 146 shown in FIG. 14. For example, when a level of the contribution ratio of "High" is chosen, q is set to be 3 (q=3), and a value of 3 times the measured value of the noise intensity ($\sigma$) ($\sigma \times 3$) is used to substitute for $\delta$ in the equation (9). When a level of the contribution ratio of "Medium" or "Low" is chosen, q is set to be 2 or 1 (q=1 or q=2), respectively, and a value of twice $\sigma$ ($\sigma \times 2$) or a is used to substitute for $\delta$ in the equation (9). The operator can also specify the contribution ratio q by inputting an arbitrary numerical value. The operator can also choose the contribution ratio according to the imaging part set on the imaging part setting region 145, or the region in the CT image such as region of the heart.

Since 99.4% of noises in a normal distribution are included in the range of $\sigma \times 3$, significant noise reduction effect can be obtained by choosing the contribution ratio of "High". However, pixel values of the imaging object about 3 times the noise intensity ($\sigma$) are also reduced, and therefore resolution of the CT image reduces. Accordingly, it is desirable that the operator changes the contribution ratio depending on the situation with understanding that the noise reduction effect and degradation of resolution are in a trade-off relationship.

In this embodiment, range of the noise reduction of a CT image can be changed depending on noise calculated for every pixel j. If the contribution ratio is the same, the ranges of noises (99.4% in the case of $3\sigma$) is also the same in a relative meaning, and therefore improvement in visibility can be expected for each pixel also for a tissue of which noise intensity level of a imaging object is different.

<Embodiment 7>

Hereafter, the X-ray CT apparatus of the embodiment 7 will be explained.

The embodiment 7 employs a configuration that noises and artifacts are detected from at least one of the CT image, corrected difference image, and noise image, and the results of the detection are used to set the parameter $\delta$ in the equation (9) of the embodiment 1.

Specifically, the noise measurement part 151 detects artifacts contained in a region of interest set in at least one of the CT image, corrected difference image, and noise image by image processing or the like, and differences of the CT values of the pixels of the artifacts, and the CT values of the pixels of the region of interest other than the artifacts are calculated as noise intensities. These noise intensities per se or the noise intensities multiplied by the predetermined contribution ratio explained in the embodiment 6 are used to substitute for $\delta$ in the equation (9).

Figure 15:
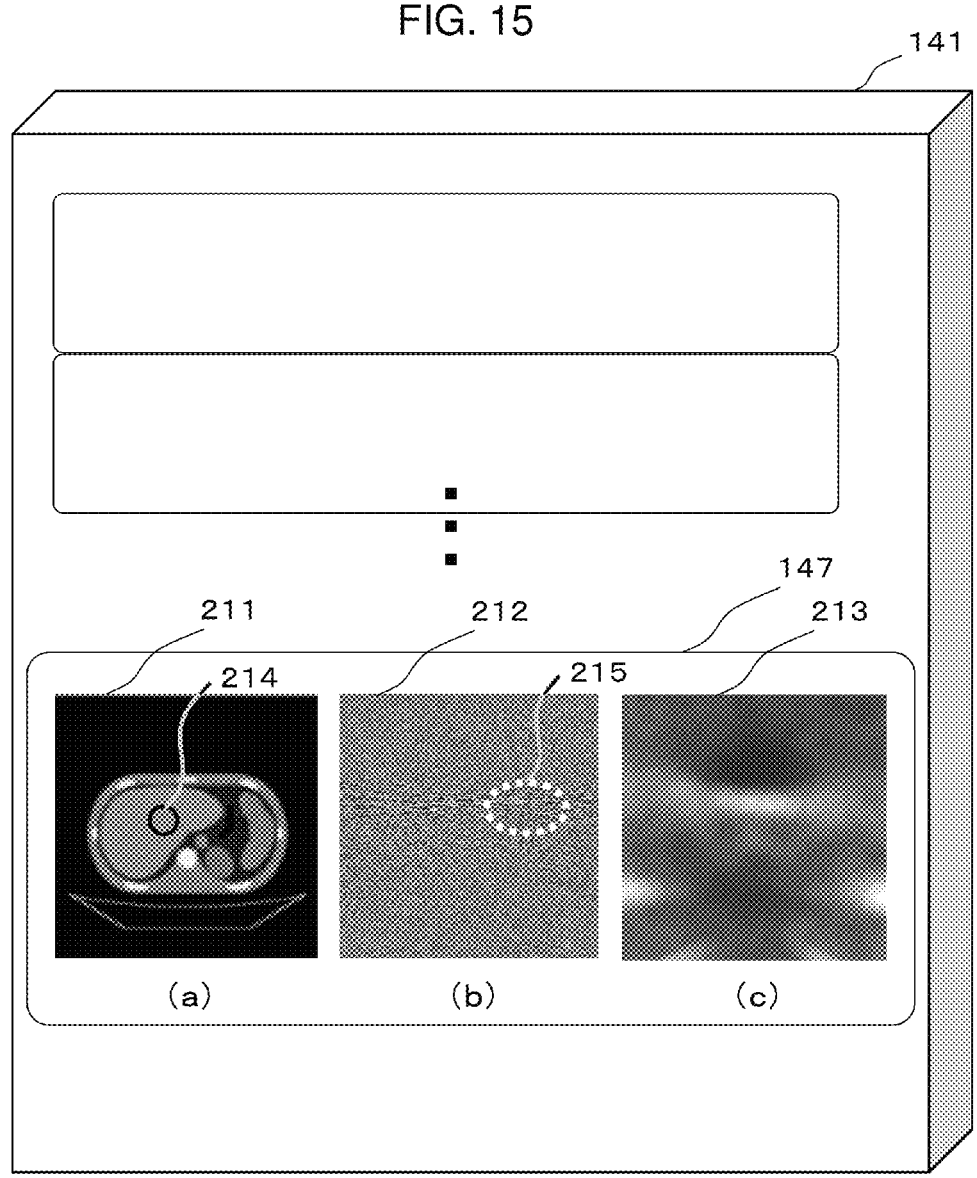
FIG. 15 is an explanatory drawing for explaining an image output region according to the embodiment 7.

For example, the imaging condition reception screen 141 of the embodiment 7 is shown in FIG. 15. The imaging condition reception screen 141 shown in FIG. 15 employs a configuration that an image output region 147 is added to the imaging condition reception screen 141 of the embodiment 1 shown in FIG. 3. On the image output region 147, at least one of a CT image 211, corrected difference image 212, and noise image 213 is displayed.

For example, if a region of interest 214 is set in the CT image 211, the noise measurement part 151 detects a pixel of high intensity from the inside of the region of interest 214 as an artifact using a known image processing technique. CT value difference of the pixel of this artifact and the pixel that is not artifact of a tissue in the region of interest 214 is calculated, and used as a noise intensity. The calculated noise intensity is set to be δ in the equation (9). With this configuration, the successive approximation processing part 152 can carry out the noise reduction processing with the noise intensity corresponding to the artifact in the region of interest 214. By detecting artifacts and noises in a region of interest 215 from the corrected difference image 212 or the noise image 213 in a similar manner, noise reduction suitable for the artifact can be performed.

As described above, according to the embodiment 7, artifacts can be directly detected, and the CT values of the pixels thereof can be used to calculate the noise intensities, in contrast to the case of detecting variation of the CT values in a region of interest (standard deviation c) as the noise intensity, as in the embodiment 1. Therefore, when an artifact of high intensity exists, that intensity can be correctly measured. Accordingly, the artifact of high intensity can be efficiently removed.

Further, if (a) the CT image 211, (b) the corrected difference image 212, and (c) the noise image 213 are displayed on the image output region 147 side by side as shown in FIG. 15, positions of borders of organs in the subject 6 can be confirmed from (a) the CT image 211, and artifacts observed as characteristic transverse lines can be confirmed in (b) the corrected difference image 212. Therefore, the regions of interest 214 and 215 can be set with confirming both (a) the CT image 211, and (b) the corrected difference image 212, and distributions of the noise intensities of the regions of interest 214 and 215 can be confirmed with (c) the noise image 213. Therefore, when the regions of interest 214 and 215 are automatically set, whether the setting positions are proper or not can be confirmed on the basis of (a) the CT image 211, (b) the corrected difference image 212, and (c) the noise image 213, and when they are manually set, the positions thereof can be adjusted with confirming whether the setting positions are proper or not.

Since the other parts of the configuration are the same as those of the embodiment 1, explanations thereof are omitted.

<Embodiment 8>

The X-ray CT apparatus of the embodiment 8 will be explained.

Although the X-ray CT apparatus of the embodiment 8 is the same as that of the embodiment 1 in that it measures noise intensities of CT image, it differs from that of the embodiment 1 in that it does not perform the successive approximate reconstruction, but reduces noise by an image processing such as data smoothing processing. If the measured projection data are divided for the projection angle direction, the accuracy of noise elimination is reduced by the influence of the reduction of accuracy of noise measurement for a region remote from the rotation center. Therefore, according to the embodiment 8, the direction for the division of the measured projection data is set to be the channel direction or slice direction for at least a region remote from the rotation center. With such a configuration, noise is accurately reduced by an image processing.

Hereafter, the X-ray CT apparatus of the embodiment 8 will be explained with reference to FIGS. 16 to 24. Although contents of some of these drawings overlap with those of the drawings used for the explanation of the embodiment 1, the drawings containing overlapping contents are used again without omitting them, in order to clarify the whole configuration of the X-ray CT apparatus of the embodiment 8. However, the same numerals are attached to the same parts of the configuration as those of the embodiment 1, and explanations thereof are omitted.

Figure 16:
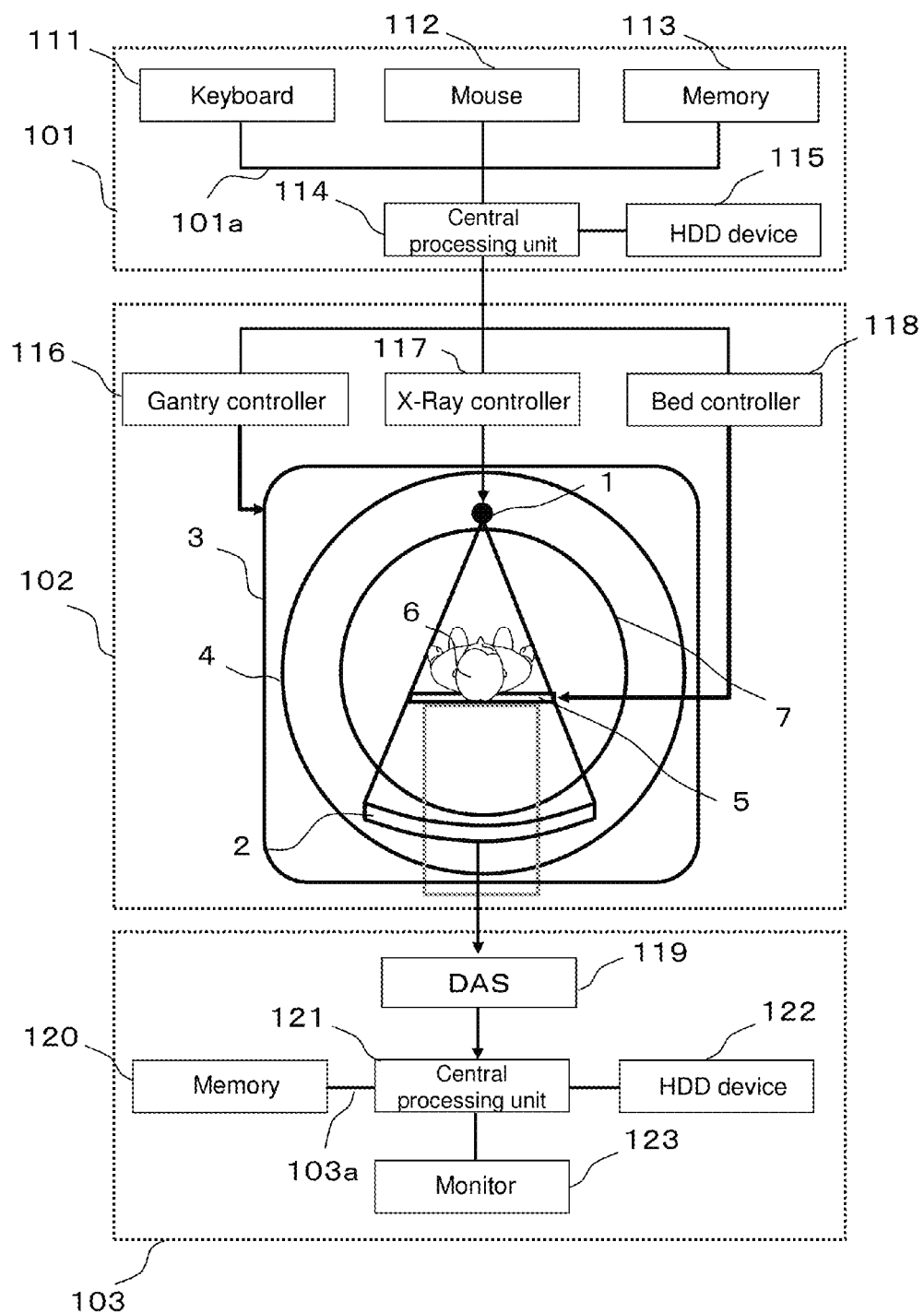
FIG. 16 is a block diagram for explaining configuration of hardware of parts of an X-ray CT apparatus according to the embodiment 8.

FIG. 16 is a drawing showing the hardware configuration of the X-ray CT apparatus of the embodiment 8. Since the hardware configuration of the X-ray CT apparatus of the embodiment 8 is the same as that of the embodiment 1 shown in FIG. 1, as shown in FIG. 16, detailed explanations thereof are omitted.

Figure 17:
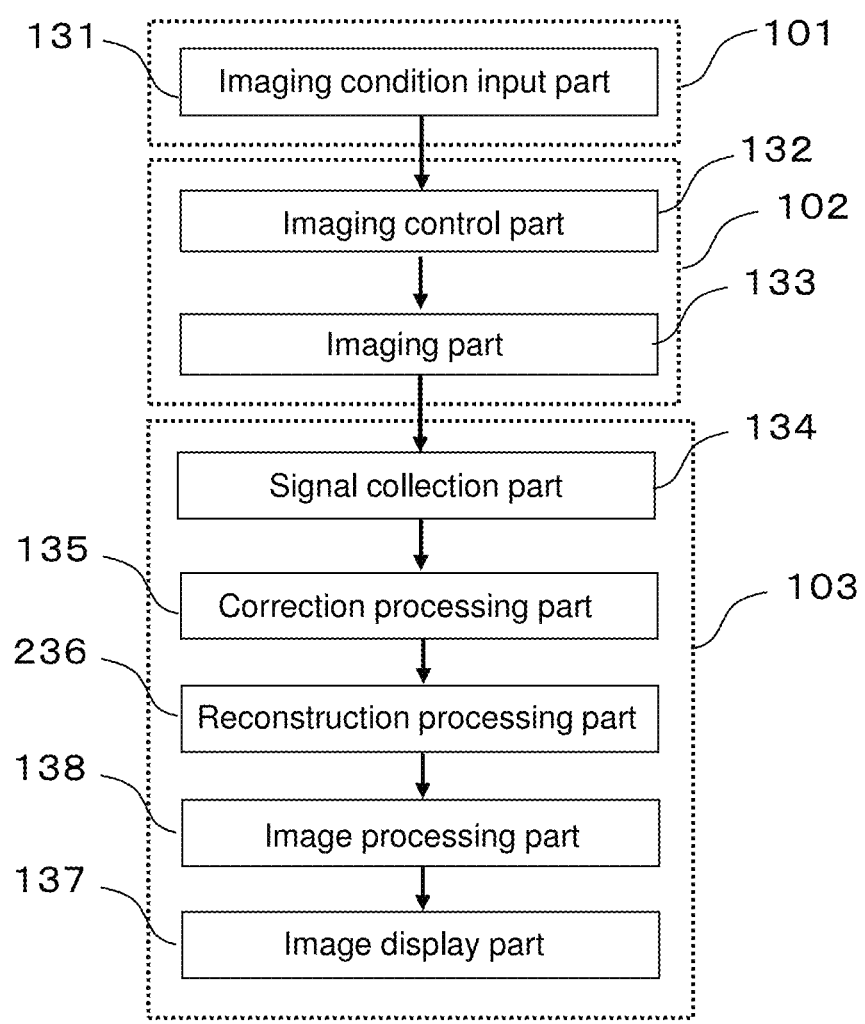
FIG. 17 is a functional block diagram of the X-ray CT apparatus according to the embodiment 8.

FIG. 17 is a functional block diagram of the X-ray CT apparatus of the embodiment 8. The input part 101 shown in FIG. 17 functions as the imaging condition input part 131 for inputting imaging conditions. The imaging part 102 functions as the imaging control part 132 that controls imaging according to the imaging conditions inputted on the imaging condition input part 131, and the imaging part 133 that performs irradiation and detection of X-rays. These functions are the same as those of the embodiment 1. The image generation part 103 functions as the signal collection part 134 that converts the detected signals into digital signals, the correction processing part 135 that corrects the digital signals, the reconstruction processing part 236 that performs image reconstruction with the corrected projection data, an image processing part 138 that performs image processing such as known data smoothing processing for the reconstructed CT image, and an image display part 137 that outputs the CT image obtained by the image processing. The functions provided in this embodiment different from those of the embodiment 1 are those of the reconstruction processing part 236 and the image processing part 138, and they are realized by the CPU 121 of the image generation part 103 by reading and executing predetermined programs stored beforehand in the memory 120, HDD device 122, or the like.

Figure 18:
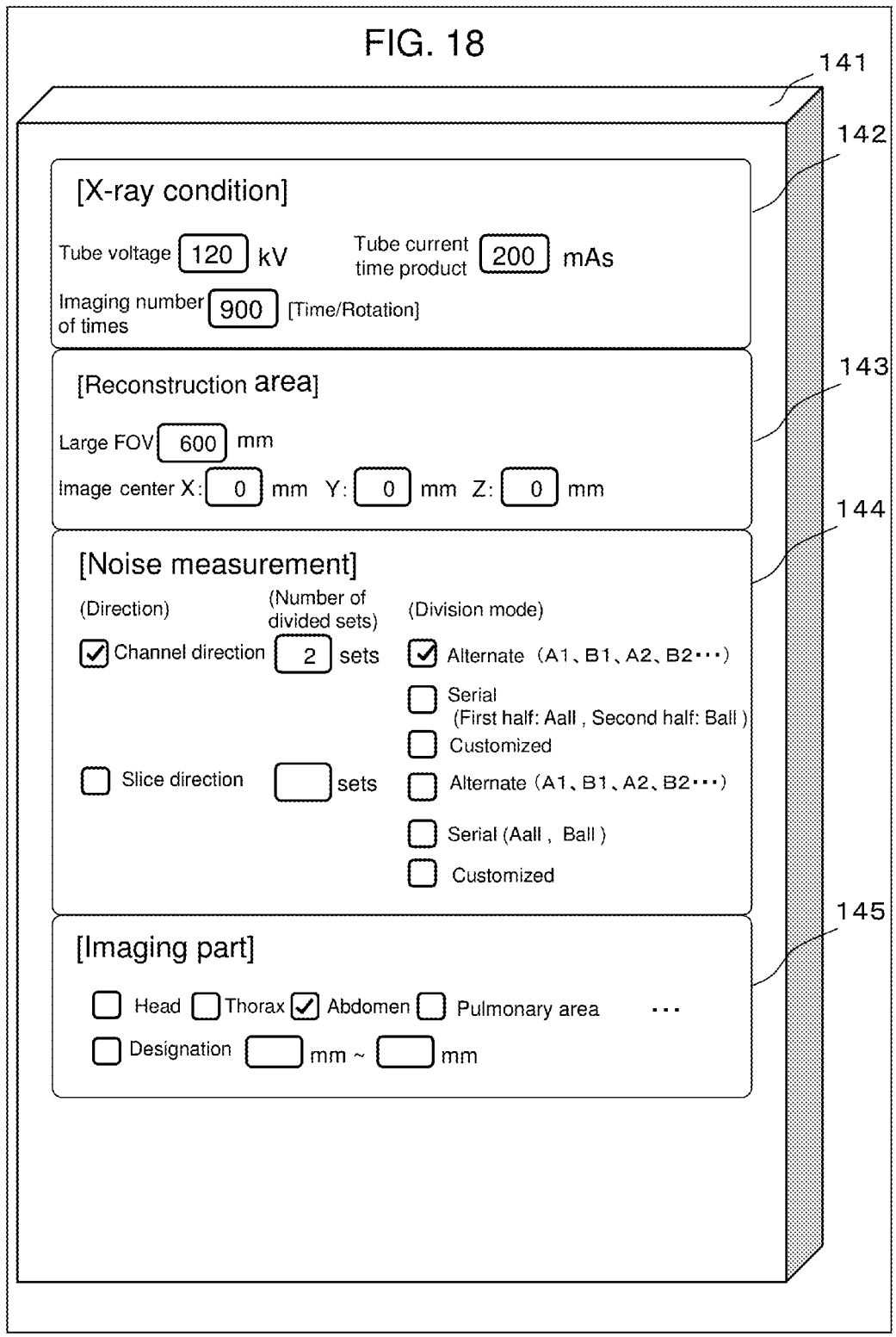
FIG. 18 is an explanatory drawing for explaining the imaging condition reception screen 141 of the imaging condition input part 131 according to the embodiment 8.

FIG. 18 is a drawing showing an example of the imaging condition reception screen 141 to be displayed on the monitor 123 of the imaging condition input part 131.

The imaging condition input part 131 displays the imaging condition reception screen 141 shown in FIG. 3 on the monitor 123, and receives input by the operator.

The imaging condition input part 131 shown in FIG. 17 displays the imaging condition reception screen 141 shown in FIG. 18 on the monitor 123, and receives input by the operator. Since the imaging condition reception screen 141 shown in FIG. 18 has the same configuration as that shown in FIG. 3 explained for the embodiment 1, detailed explanations thereof are omitted here.

Then, the imaging control part 132 and the imaging part 133 shown in FIG. 17 perform X-ray imaging according to the imaging conditions received by the imaging condition input part 131. The signal collection part 134 shown in FIG. 17 obtains the output signals of the X-ray detector 2, and the correction processing part 135 performs correction processing to obtain measured projection data. These processings are the same as those used in the embodiment 1.

Figure 19:
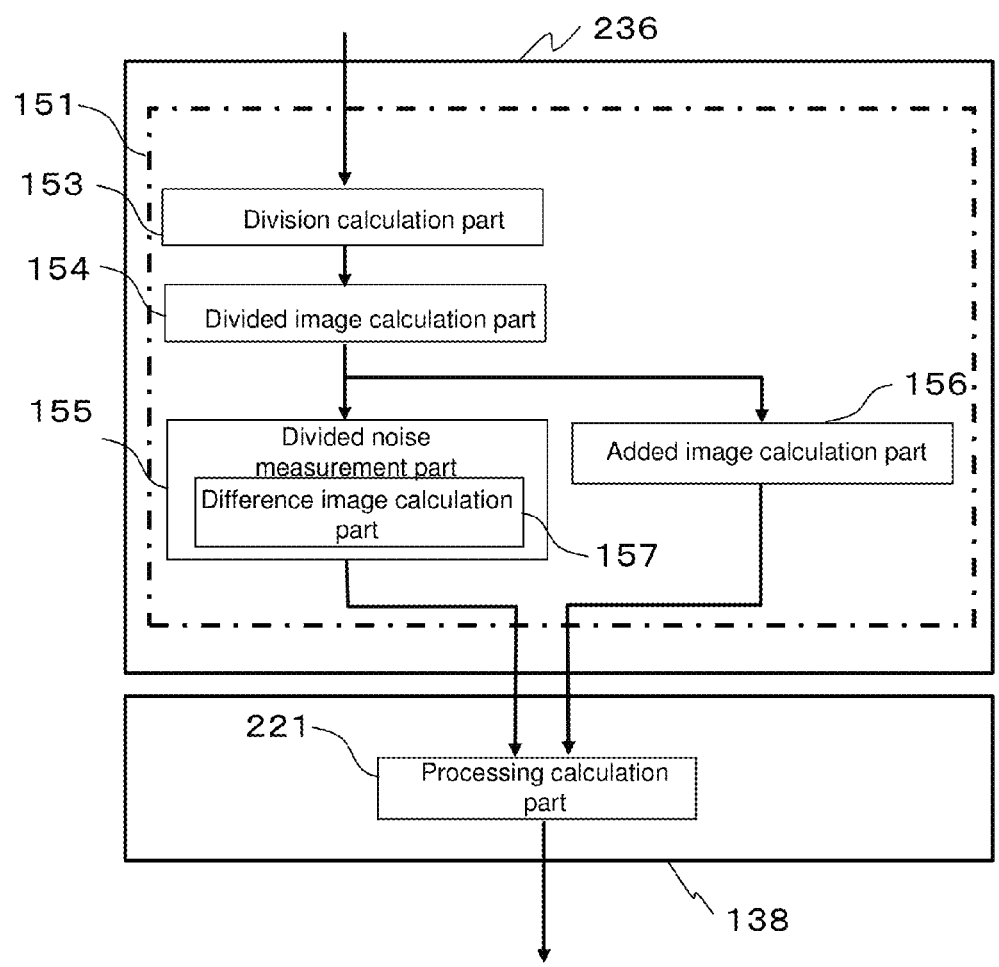
FIG. 19 is a functional block diagram for explaining the functions of the reconstruction processing part 236, and the image processing part 138 according to the embodiment 8.

The detailed functional configurations of the reconstruction processing part 236 and the image processing part 138 are shown in FIG. 19. The reconstruction processing part 236 comprises the noise measurement part 151 that measures noise of the CT image. The image processing part 138 comprises a processing calculation part 221 that performs image processing for removing noise of the CT image using the measured noise intensities.

Figure 20:
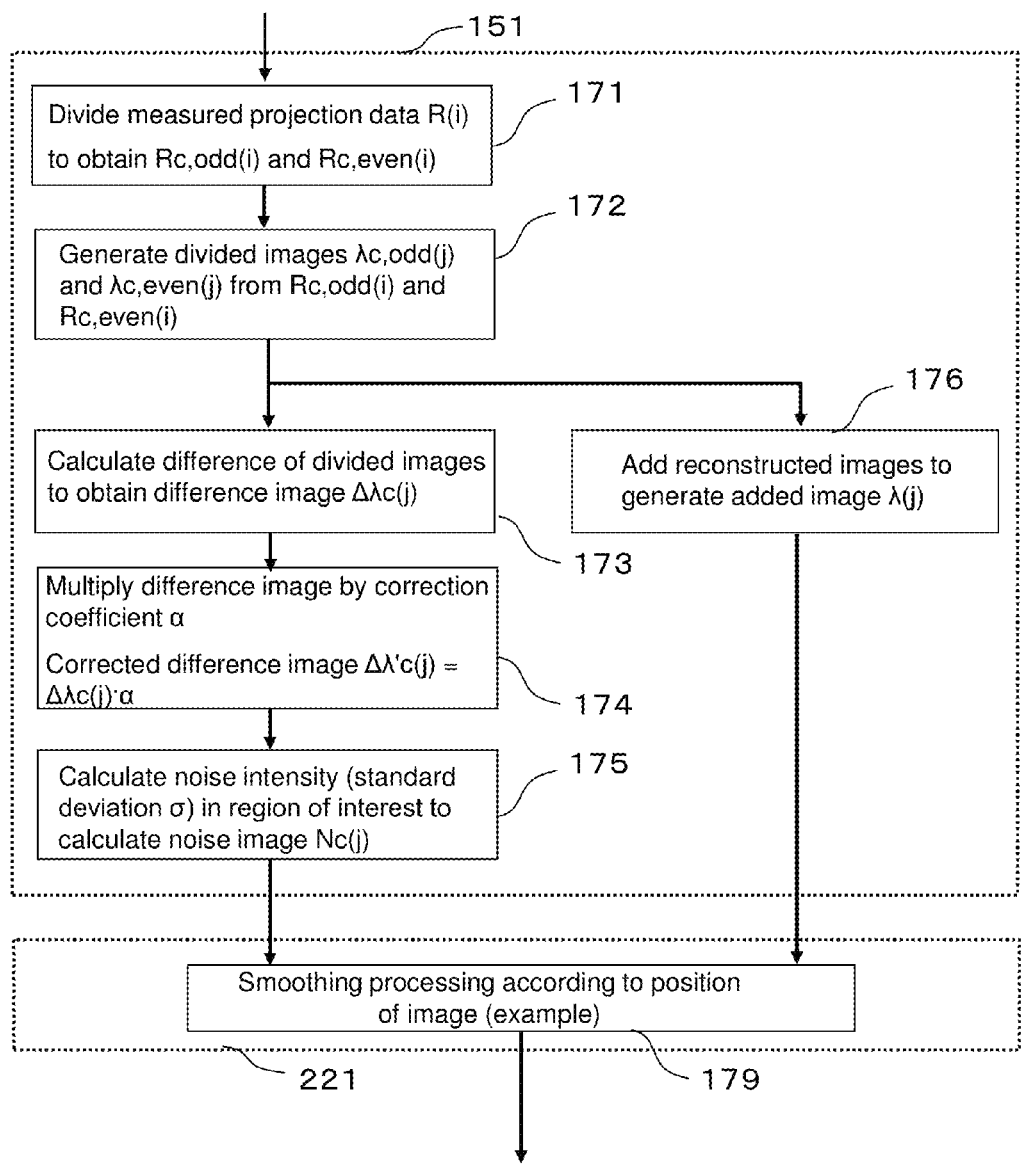
FIG. 20 is a flowchart for explaining calculation procedure performed by the noise measurement part 151 according to the embodiment 8.
Figure 21:
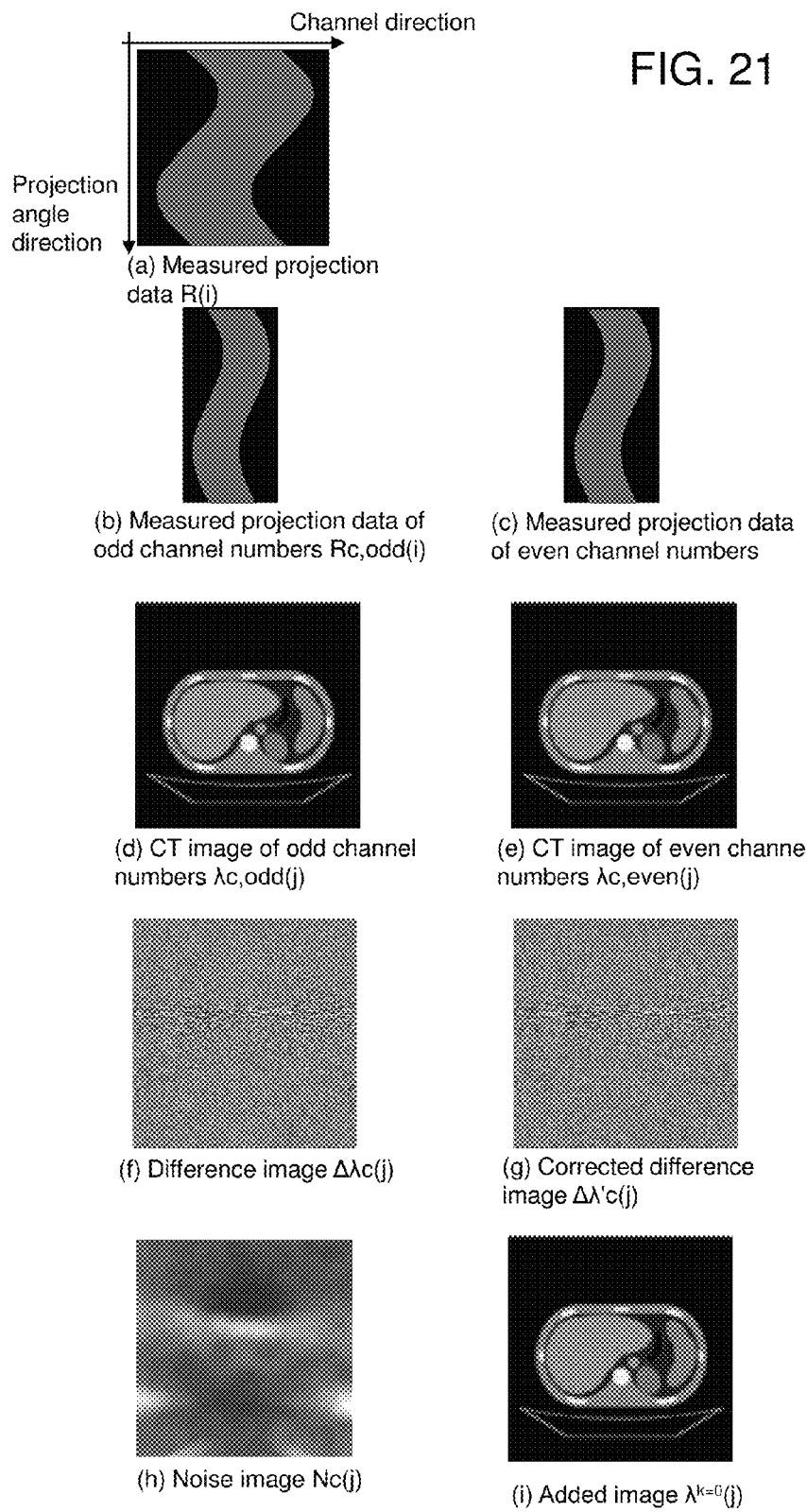
FIGS. 21, (a) to (i) are the explanatory drawings for explaining the results of the calculation performed by the noise measurement part 151 according to the embodiment 8.

The functional configuration of the noise measurement part 151 and operation thereof are the same as those of the embodiment 1 as shown in FIGS. 19, 20, and 21, and the measured projection data R(i) (FIG. 21, (a)) are divided for the channel direction or slice direction to obtain divided measured projection data $R_{c,odd}(i)$ and $R_{c,even}(i)$ (FIGS. 21, (b) and (c)) through the steps 171 to 175 shown in FIG. 20. These data are used for reconstruction to generate divided images $A_{c,odd}(j)$, and $A_{c,even}(j)$ (FIGS. 21, (d) and (e)), respectively. A difference image Δλ$_c$(j) of the divided images is obtained (FIG. 21, (f)), and then corrected to obtain a corrected difference image Δλ'$_c$(j) (FIG. 21, (g)), a region of interest is set, and the standard deviation σ is obtained as noise intensity. The region of interest is shifted, and noise intensities are detected to generate a noise image N$_c$(j) (FIG. 21, (h)). Further, in the step 176 shown in FIG. 20, the divided images are added according to the equation (13) in the added image calculation part 156 to also generate an added image λ(j) (FIG. 21, (i)).

[Equation 13]

$$\lambda(j) = \frac{\lambda_{c,odd}(j) + \lambda_{c,even}(j)}{2} \quad (13)$$

The added image λ(j) is equivalent to a CT image obtained by performing reconstruction processing of the measured projection data. The processing calculation part 221 of the image processing part 138 selectively reduces the noise of the CT image by using the noise intensities calculated by the noise measurement part 151 in the step 179 shown in FIG. 20. By this procedure, degradation of CT values other than those of the noise of the CT image, for example, those of the image of the imaging object, is prevented.

Hereafter, the processing performed by the processing calculation part 221 will be explained. As the processing performed by the processing calculation part 221, data smoothing processing based on a known Gaussian function can be used. By this processing, spatial filtering is performed by using a weighted matrix in which weight is varied. The Gaussian function includes the standard deviation a that represents spread as a parameter, and the degree of the smoothing, or the spatial resolving power of the image can be adjusted by changing the value of σ. In the case of a two-dimensional image λ(x, y), the calculation for the smoothing using a Gaussian function is performed according to the equation (14). The equation (14) represents a two-dimensionally isotropic Gaussian function, in which average is 0, and the standard deviation is σ.

[Equation 14]

$$G(x, y) = \frac{1}{2\pi\sigma^2} \exp\left\{-\frac{x^2 + y^2}{2\sigma^2}\right\} \quad (14)$$

By convolution of G(x,y) and λ(x,y), a smoothened image F(x,y) is obtained as shown by the equation (15).

[Equation 15]

$$F(x, y) = G(x, y) * \lambda(x, y) = \int\int_{-\infty}^{\infty} f(\alpha, \beta) G(x-\alpha, y-\beta) \, d\alpha \, d\beta \quad (15)$$

In this embodiment, the standard deviation σ (pixel value of the noise image N$_c$(j)) detected as the noise intensity calculated by the noise measurement part 151 shown in FIG. 20 is used to substitute for σ in the equation (14). The noise of the CT image can be thereby selectively processed by using the measured noise intensities. Degradation of CT values other than those of noise, for example, those of the image of imaging object, can be thereby prevented. For example, when the noise intensity (σ) is high, the effect of the smoothing becomes more significant, and an image is generated with lower spatial resolving power. Therefore, an image representing the general structure of the imaging object can be generated without being influenced by the noise. On the other hand, when the noise intensity (σ) is low, the effect of the smoothing becomes less significant, the spatial resolving power is not significantly degraded, and an image that enables grasp of detailed shape of the imaging object can be generated.

Since the other parts of the configuration and processings are the same as those of the embodiment 1, explanations thereof are omitted.

Figure 22:
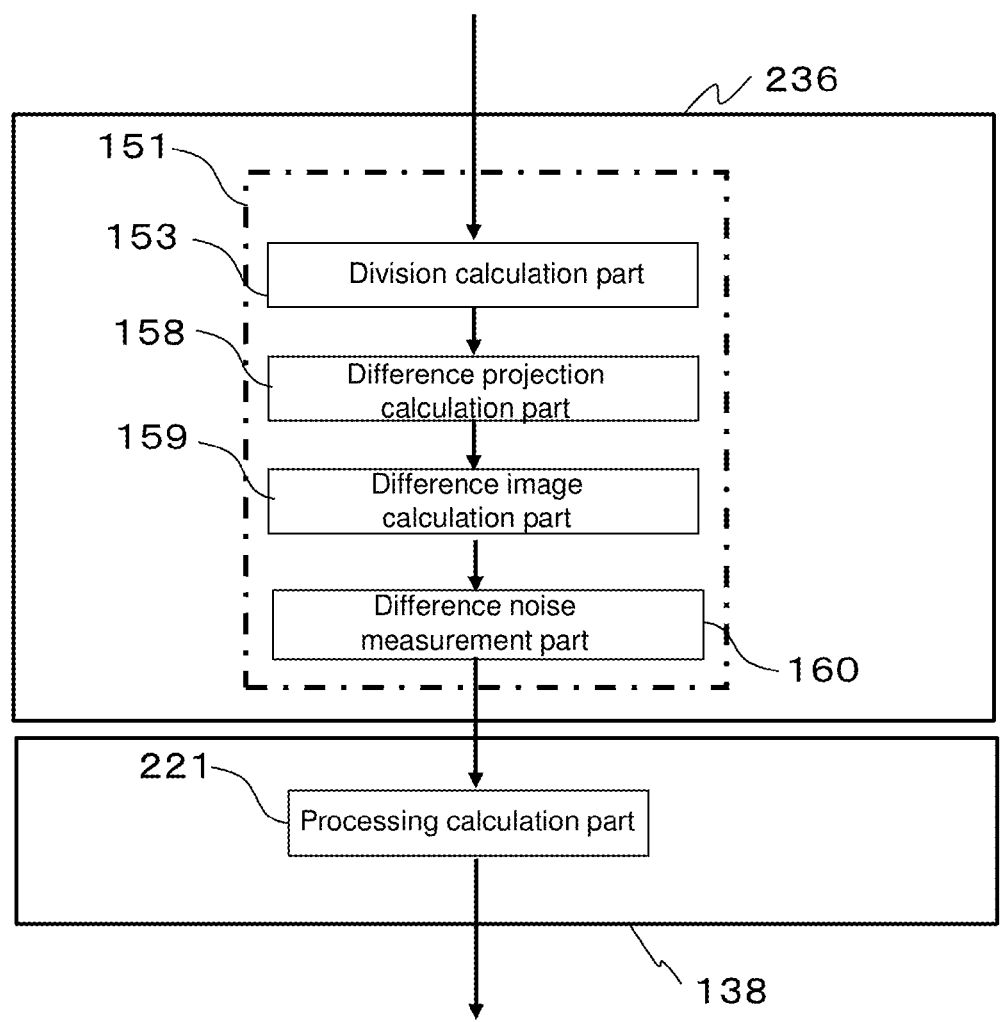
FIG. 22 is a functional block diagram for explaining the functions of the reconstruction processing part 236, and the image processing part 138 of another example according to the embodiment 8.

The aforementioned embodiment 8 employs a processing configuration that the noise measurement part 151 divides the measured projection data for the channel direction or slice direction, reconstruction is performed, and then difference is obtained. However, as explained for the embodiment 2, it is also possible to use the method of obtaining the difference of two or more kinds of divided measured projection data, and reconstruct the difference measured projection data obtained by the difference processing to obtain a difference image. Specifically, as shown in FIG. 22, as the functional configuration of the noise measurement part 151, the same configuration as that of the embodiment 2 shown in FIG. 9 is used. Since the detailed configuration of the noise measurement part 151 shown in FIG. 22 is the same as that of the embodiment 2, explanation thereof is omitted.

Further, the direction for the division of the measured projection data performed by the noise measurement part 151 is not limited to one of the channel direction and the slice direction, and it is also possible to employ a configuration that the direction for the division of the measured projection data is chosen according to the position of the region of interest on the CT image, as used in the embodiment 3. Specifically, there can be employed a configuration that when the region of interest locates within a predetermined area relative to the position in the CT image corresponding to the rotation center of the rotation plate, the noise measurement part 151 chooses the projection angle direction as the direction for the division of the measured projection data, and when the region of interest locates outside the predetermined area, it chooses the channel direction or the slice direction as the direction for the division.

Figure 23:
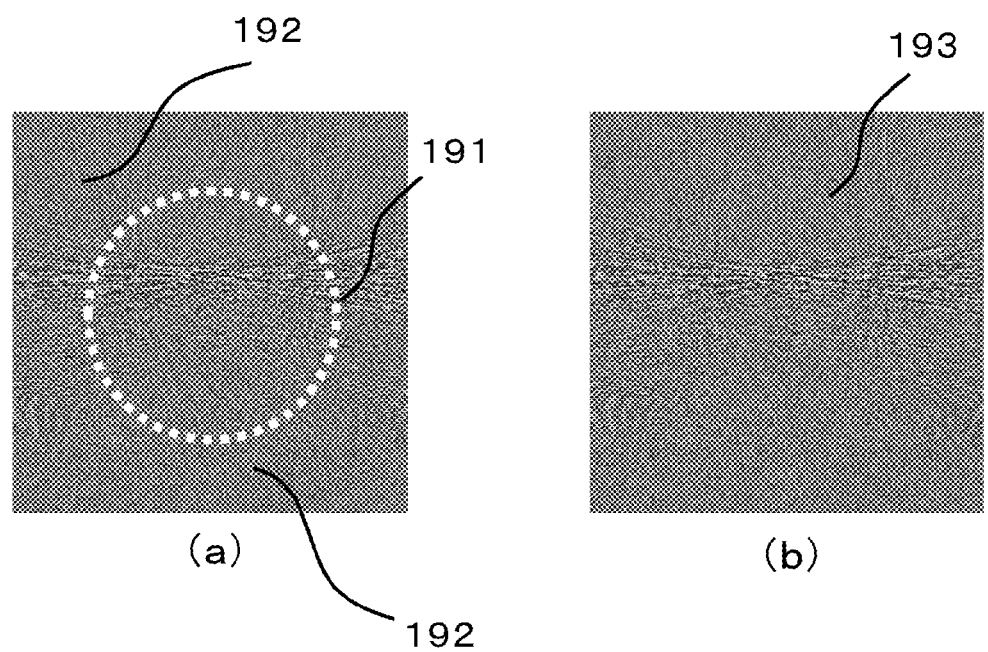
FIG. 23 includes explanatory drawings showing corrected difference images calculated from the measured projection data divided for (a) projection angle direction and (b) channel direction, and regions thereof according to the embodiment 8.

For example, an example of the corrected difference image calculated from the measured projection data divided for the projection angle direction is shown in FIG. 23, (a). With a usual number of times of imaging per rotation, an artifact of high intensity is generated in the outer region 192 defined by the line 191 shown in FIG. 23, (a) as the border. On the other hand, when the measured projection data are equally divided for the channel direction, the measurement errors of noise intensity are uniformly generated over the entire region 193 of the corrected difference image, irrespective of the position of the region of interest in the CT image, as shown in FIG. 23, (b).

Figure 24:
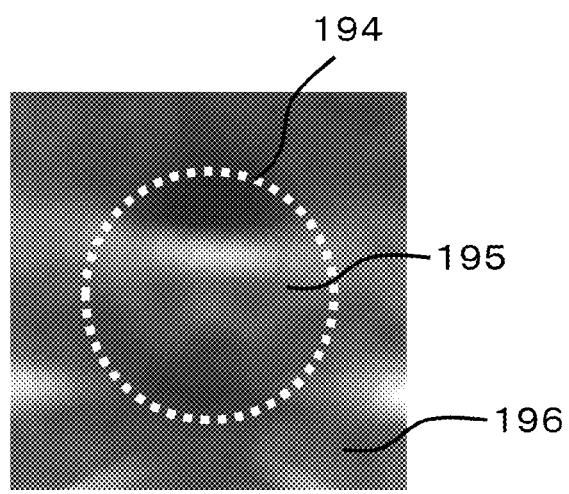
FIG. 24 is an explanatory drawing showing a noise image obtained with choosing the projection angle direction or the channel direction for each region in a CT image and the region thereof according to the embodiment 8.

Therefore, also in this embodiment 8, the CT image may be divided into regions as in the embodiment 3, and as shown in the noise image of FIG. 24, noise intensity obtained by setting the direction for the division to be the projection angle direction is used for the center region 195 inside the line 194 that locates a predetermined distance from the position corresponding to the rotation center of the rotation plate 4, whereas noise intensity obtained by setting the direction for the division to be the channel direction or the slice direction is used for the outer region 196. As the radius r of the line 194, a predetermined value may be used, or a value inputted by the operator from the imaging condition input part 131 may be used. Since the detailed configuration and processing method are the same as those of the embodiment 3, explanations thereof are omitted here.

By choosing the direction for the division according to the position of the region of interest in the CT image as described above, accuracy of the noise intensity measurement can be enhanced.

As another configuration, there can also be employed a configuration that the noise measurement part 151 chooses at least two directions from the channel direction, slice direction, and projection angle direction, the noise intensities obtained from division for each direction are weighted, and added, and the sum is use as the noise intensity. The value of weight is changed according to the position of the region of interest in the CT image. By changing the weight depending on the position of the region of interest in the CT image as described above, accuracy of the noise intensity measurement can be enhanced. Since the detailed configuration and processing method are the same as those of the embodiment 3, explanations thereof are omitted here.

The data smoothing processing using the Gaussian function represented by the equation (15) used in the embodiment 8 is an example, and a known image processing method based on the known thresholding processing can of course be also used.

The X-ray CT apparatus of the embodiment 8 is not limited to an apparatus of the aforementioned configuration, and the various variations described for the embodiment 1 can be applied to the apparatus of the embodiment 8.

DESCRIPTION OF NUMERICAL NOTATIONS

1 . . . X-Ray tube, 2 . . . X-ray detector, 3 . . . gantry, 4 . . . rotation plate, 5 . . . bed, 6 . . . imaging object, 7 . . . circular opening, 101 . . . input part, 102 . . . imaging part, 103 . . . image generation part, 111 . . . keyboard, 112 . . . mouse, 113 . . . memory, 114 . . . central processing unit, 115 HDD device, 116 . . . gantry controller, 117 . . . X-ray controller, 118 . . . bed controller, 119 . . . DAS, 120 . . . memory, 121 . . . central processing unit, 122 . . . HDD device, 123 . . . monitor, 131 . . . imaging condition input part, 132 . . . imaging control part, 133 . . . imaging part, 134 . . . signal collection part, 135 . . . correction processing part, 136 . . . successive approximate reconstruction part, 137 . . . image display part, 138 . . . image processing part, 141 . . . imaging condition reception screen, 142 . . . X-ray condition setting region, 143 . . . reconstruction area setting region, 144 . . . noise measurement setting region, 145 . . . imaging part setting region, 146 . . . contribution ratio setting region, 147 . . . image output region, 151 . . . noise measurement part, 152 . . . successive approximation processing part, 153 . . . division calculation part, 154 . . . divided image calculation part, 155 . . . divided noise measurement part, 156. . . added image calculation part, 157 . . . difference image calculation part, 158 . . . fan beam/parallel beam conversion part, 161 . . . analytical reconstruction part, 162 . . . forward projection part, 163 . . . difference calculation part, 164 . . . back projection processing part, 165 . . . prior calculation part, 166 . . . image correction part, 167 . . . fan beam/parallel beam conversion part, 191 . . . line (border) in noise image for channel direction and projection angle direction, 192 . . . outer region, 193 . . . corrected difference image for channel direction, 194 . . . line (border) in noise image for channel direction and projection angle direction, 195 . . . noise image for projection angle direction, 196 . . . noise image for channel direction, 201 . . . region of interest (circle), 202 . . . region of interest around spinal cord, 211 . . . CT image, 212 . . . corrected difference image, 213 . . . noise image, 214. . . region of interest, 215 . . . region of interest, 221 . . . processing calculation part, 236 . . . reconstruction processing part

The invention claimed is:

1. An X-ray CT apparatus comprising:
an X-ray generation part that generates X-rays,
an X-ray detection part that detects X-rays that transmit through an imaging object, and obtains measured projection data,
a rotation plate that carries the X-ray generation part and the X-ray detection part, and rotates around the imaging object, and
a successive approximate reconstruction part that reconstructs a CT image from the measured projection data obtained by the X-ray detection part for a reconstruction area of the imaging object, obtains calculated projection data by performing forward projection of the CT image by calculation, and successively corrects the CT image so that the calculated projection data and the measured projection data become equal to each other,
wherein the successive approximate reconstruction part comprises a noise measurement part that calculates noise intensity in the CT image for at least a predetermined region of interest, and successively corrects the region of interest of the CT image by using the noise intensity calculated by the noise measurement part,
wherein the noise measurement part includes:
a division calculation part that divides the measured projection data into M sets of measured projection data,
a divided image calculation part that reconstructs a CT image for each of the M sets of the measured projection data divided by the division calculation part, and
a divided noise measurement part that obtains a difference image of the M sets of the CT images reconstructed by the divided image calculation part, and calculates a variation of the CT values of the region of interest in the difference image as the noise intensity,
wherein the X-ray detection part contains a plurality of X-ray detection elements disposed along a channel direction and a slice direction, and the X-ray detection part detects the X-rays at a plurality of projection angles while the rotation plate rotates one time,
wherein the division calculation part divides the measured projection data for at least two directions among the channel direction, the slice direction, and a projection angle direction, and
wherein the noise measurement part chooses at least two directions for the division of the measured projection data performed by the division calculation part from the channel direction, the slice direction, and the projection angle direction, uses a sum of noise intensities obtained and weighted for the respective directions as the noise intensity, and changes weights according to the position of the region of interest in the CT image.

2. The X-ray CT apparatus according to claim 1, wherein the successive approximate reconstruction part repeatedly performs calculation for correcting the CT image by using a difference of the measured projection data and the calculated projection data so that the difference becomes smaller, and prior calculation for correcting the CT image by using a difference of CT values of two or more of pixels of the CT image before the correction so that the difference of the CT values becomes smaller, and in the prior calculation, corrects the CT image in the region of interest by using the noise intensity of the region of interest calculated by the noise measurement part.

3. The X-ray CT apparatus according to claim 2, wherein the noise measurement part calculates a distribution of the noise intensity for the whole CT image by setting a plurality of regions of interest for the CT image, and calculating the noise intensity for each of the regions of interest, and generates a noise image that represents the distribution of the noise intensity.

4. The X-ray CT apparatus according to claim 2, wherein, in the prior calculation, the successive approximate reconstruction part changes correction amount of a CT value of a predetermined first pixel in the region of interest according to a magnitude relationship of difference of CT values of the first pixel and a second pixel in a predetermined positional relationship with respect to the first pixel, and the noise intensity obtained for the region of interest.

5. The X-ray CT apparatus according to claim 4, wherein, when the difference of CT values of the first pixel and the second pixel is smaller than the noise intensity obtained for the region of interest, the successive approximate reconstruction part corrects the CT value of the first pixel by a correction amount corresponding to an absolute value of the difference of the CT values, and, when the difference of the CT values is larger than the noise intensity, the successive approximate reconstruction part corrects the CT value of the first pixel by a predetermined correction amount irrespective of the difference of the CT values.

6. The X-ray CT apparatus according to claim 2, wherein, in the prior calculation, the successive approximate reconstruction part changes a correction amount of a CT value of a predetermined first pixel in the region of interest according to magnitude relationship of difference of CT values of the first pixel and a second pixel in a predetermined positional relationship with respect to the first pixel, and a value obtained by multiplying the noise intensity obtained for the region of interest by a predetermined contribution ratio.

7. The X-ray CT apparatus according to claim 1, wherein:
the noise measurement part comprises:
a difference projection calculation part that obtains difference projection data by calculating a difference of the M sets of the measured projection data divided by the division calculation part, and
a difference image calculation part that obtains a difference image by image reconstruction from the difference projection data.

8. The X-ray CT apparatus according to claim 1, wherein:
the noise measurement part detects an artifact contained in the region of interest of the CT image, and calculates a difference of a CT value of a pixel of the artifact, and a CT value of a pixel that is not a pixel of the artifact in the region of interest as the noise intensity.

9. The X-ray CT apparatus according to claim 1, wherein:
the division calculation part divides the measured projection data into M sets of the measured projection data for at least one direction among the channel direction and the slice direction.

10. The X-ray CT apparatus according to claim 1, wherein:
the noise measurement part chooses the directions for the division of the measured projection data performed by the division calculation part according to a position of the region of interest in the CT image.

11. The X-ray CT apparatus according to claim 10, wherein:
when the region of interest is located in a predetermined area with respect to the position in the CT image corresponding to the rotation center of the rotation plate, the noise measurement part chooses the projection angle direction as one of the directions for the division of the measured projection data, and when the region of interest is located outside of the predetermined area, the noise measurement part chooses the channel direction or the slice direction as one of the directions for the division.

12. The X-ray CT apparatus according to claim 1, wherein:
the X-ray generation part irradiates X-rays as a fan beam to the X-ray detection part, and
the noise measurement part comprises a fan beam/parallel beam conversion part for converting the measured projection data obtained with the fan beam and divided by the division calculation part into measured projection data of parallel X-ray paths.

13. The X-ray CT apparatus according to claim 1, wherein:
the noise measurement part comprises an image addition part that adds two or more CT images among the M sets of the CT images reconstructed by the divided image calculation part, and
the successive approximate reconstruction part uses the CT image obtained by the addition performed by the image addition part as an initial image for the successive correction of the CT image.

14. The X-ray CT apparatus according to claim 1, wherein:
the successive approximate reconstruction part sets the region of interest to be in a shape corresponding to a shape of a tissue in the imaging object.

* * * * *